(12) United States Patent
Carusillo et al.

(10) Patent No.: US 8,403,932 B2
(45) Date of Patent: Mar. 26, 2013

(54) INTEGRATED CUTTING GUIDE AND SAGITTAL SAW BLADE ASSEMBLY

(75) Inventors: Steven Carusillo, Kalamazoo, MI (US);
Gregory E. Plaskon, Clifton, NJ (US);
Carlos E. Collazo, Old Greenwich, CT (US); Alessandro F. Canonaco, Caldwell, NJ (US); Eric Rugo, Allentown, NJ (US); David J. Neal, Oak Ridge, NJ (US)

(73) Assignee: Stryker Corporation, Kalamazoo, MI (US)

( * ) Notice: Subject to any disclaimer, the term of this patent is extended or adjusted under 35 U.S.C. 154(b) by 58 days.

(21) Appl. No.: 13/102,382

(22) Filed: May 6, 2011

(65) Prior Publication Data
US 2011/0208197 A1 Aug. 25, 2011

Related U.S. Application Data

(62) Division of application No. 12/334,886, filed on Dec. 15, 2008, now Pat. No. 8,043,292, which is a division of application No. 10/887,642, filed on Jul. 9, 2004, now Pat. No. 7,497,860.

(51) Int. Cl.
*A61B 17/00* (2006.01)
(52) U.S. Cl. .......................................... 606/82; 606/88
(58) Field of Classification Search .................. 606/79, 606/82, 176, 178, 167; 30/277.4, 166.3, 30/187, 392–394, 43.7, 43.8
See application file for complete search history.

(56) References Cited

U.S. PATENT DOCUMENTS

| | | | |
|---|---|---|---|
| 1,201,467 | A | 10/1916 | Hoglund |
| 1,543,195 | A | 6/1925 | Thugesen et al. |
| 2,702,550 | A | 2/1955 | Rowe |
| 2,854,981 | A | 10/1958 | Morrison |
| 3,495,590 | A | 2/1970 | Zeiller |
| 3,642,002 | A | 2/1972 | Otterstrom |
| 3,678,934 | A | 7/1972 | Warfield et al. |
| 3,734,652 | A | 5/1973 | Barnett |
| 3,797,497 | A | 3/1974 | Crim et al. |
| 3,835,859 | A | 9/1974 | Roberts et al. |
| 3,882,737 | A | 5/1975 | Crim et al. |
| 3,905,105 | A | 9/1975 | Tuke |

(Continued)

FOREIGN PATENT DOCUMENTS

| | | |
|---|---|---|
| CH | 654 196 | 10/1991 |
| DE | 354 343 | 6/1922 |

(Continued)

OTHER PUBLICATIONS

"BIOMET Orthodedics, Inc., Flyer re "Live Surgery Webcast Microplasty Minimally Invasive Program," 2004 (1 page).".

(Continued)

*Primary Examiner* — Andrew Yang

(57) ABSTRACT

A surgical sagittal saw blade and a complementary cutting guide for use with the blade. The blade includes a bar shaped to be releasably secured in a static position to a complementary surgical sagittal saw. A blade head with teeth is mounted to the bar to pivot. One or more drive links connected to the saw extend to the blade head to pivot the blade head. The cutting guide and blade bar have complementary features for holding the blade bar to above a surface of the cutting guide. The features that hold the blade bar to the cutting guide allow the blade to move over the cutting guide surface while constrain the blade from moving out of the plane immediately above the cutting guide surface.

21 Claims, 20 Drawing Sheets

U.S. PATENT DOCUMENTS

| | | | |
|---|---|---|---|
| 3,978,862 A | 9/1976 | Morrison | |
| 4,019,408 A | 4/1977 | Idel | |
| 4,184,804 A | 1/1980 | Inagaki et al. | |
| 4,203,444 A | 5/1980 | Bonnell et al. | |
| 4,217,964 A | 8/1980 | Eaton | |
| 4,246,902 A | 1/1981 | Martinez | |
| 4,273,169 A | 6/1981 | Baenen | |
| 4,274,414 A | 6/1981 | Johnson et al. | |
| 4,461,296 A | 7/1984 | Hodge | |
| 4,502,184 A | 3/1985 | Karubian | |
| 4,513,742 A | 4/1985 | Arnegger | |
| 4,584,999 A | 4/1986 | Arnegger | |
| 4,637,391 A | 1/1987 | Schlein | |
| 4,683,924 A | 8/1987 | Cornelius | |
| 4,700,702 A | 10/1987 | Nilsson | |
| 4,892,093 A | 1/1990 | Zarnowski et al. | |
| 5,014,430 A | 5/1991 | Wortham | |
| 5,092,869 A | 3/1992 | Waldron | |
| 5,100,506 A | 3/1992 | Sturtevant et al. | |
| 5,133,728 A | 7/1992 | Petersen | |
| 5,135,533 A | 8/1992 | Petersen et al. | |
| 5,178,626 A | 1/1993 | Pappas | |
| 5,306,285 A | 4/1994 | Miller et al. | |
| 5,349,754 A | 9/1994 | Wuensch et al. | |
| 5,439,472 A | 8/1995 | Evans et al. | |
| 5,468,247 A | 11/1995 | Matthai et al. | |
| 5,496,325 A | 3/1996 | McLees | |
| 5,725,530 A | 3/1998 | Popken | |
| 5,735,866 A | 4/1998 | Adams et al. | |
| 5,817,097 A | 10/1998 | Howard et al. | |
| 5,846,244 A | 12/1998 | Cripe | |
| 6,105,535 A | 8/2000 | Atamian et al. | |
| 6,113,618 A | 9/2000 | Nic | |
| 6,875,222 B2 | 4/2005 | Long et al. | |
| 2002/0198556 A1 | 12/2002 | Ark et al. | |

FOREIGN PATENT DOCUMENTS

| | | |
|---|---|---|
| DE | 478 354 | 3/1927 |
| DE | 24 00 696 | 1/1974 |
| DE | 26 11 720 | 9/1977 |
| DE | 26 28 131 | 12/1977 |
| DE | 2 640 267 | 5/1978 |
| DE | 26 15 301 | 5/1978 |
| DE | 29 35 732 | 3/1984 |
| DE | 36 40 516 C1 | 11/1986 |
| DE | 36 38 404 A1 | 5/1988 |
| DE | 89 06 511.5 U | 8/1989 |
| DE | 41 40 395 A1 | 6/1993 |
| EP | 1 880 682 B1 | 4/2010 |
| RU | 2 218 112 | 9/2001 |
| WO | 2004/105623 | 12/2004 |

OTHER PUBLICATIONS

"BIOMET Orthopedics, Inc., Brochure re "Microplasty Minimally Invasive Knee Instruments; Surgical Technique for the Maxim, Ascent TM and Vanguard TM Total Knee Systems," 2004 (15 pages).".

"EPO ISA Search Report and Written Opinion for PCT App. No. PCT/US2006/023769, Feb. 2006."

"Invitation to Pay Additional Fees, mailed Nov. 17, 2005, in PCT/US2005/023769, with Communication Relating to the Results of the Partial International Search (7 pages)."

Stryker Corporation, "Opposition Against EP Pat. No. 1 880 682", Jan. 2011.

"William C. Schroer, M.D., Interim Report, "Minimally Invasive Knee Replacement Surgery," BIOMET Ascent, date unknown (2 pages)."

INTEGRATED CUTTING GUIDE AND SAGITTAL SAW BLADE ASSEMBLY

This Application is a divisional of U.S. Pat. App. Ser. No. 12/334,886 filed 15 Dec. 2008, now U.S. Pat. No. 8,043,292. application Ser. No. 12/334,886 is a divisional of U.S. Pat. App. Ser. No. 10/887,642, filed 9 Jul. 2004, now U.S. Pat. No. 7,497,860. The contents of the applications from which this application claims priority are explicitly incorporated herein by reference.

FIELD OF THE INVENTION

This invention is related generally to a surgical sagittal saw. More particularly, this invention is related to a surgical sagittal saw that minimally vibrates when used, does not excessively wear the cutting guide with which it is used and that has a complementary cutting guide that is relatively small in size.

BACKGROUND OF THE INVENTION

A sagittal saw is a powered surgical tool that is often used in an orthopedic surgical procedure. A sagittal saw generally includes a handpiece that houses a motor and the complementary control circuit that regulates the actuation of the motor. Extending forward, distally, from the handpiece, is a planar saw blade. The most forward end of the saw blade is formed with teeth for cutting hard tissue against which the blade is applied. A drive mechanism internal to the housing transfers the power developed by the motor to the blade. More particularly, the drive mechanism converts the rotary motion produced by the output shaft of the motor to the blade so that the blade moves in an oscillatory, back-and-forth pattern in the plane in which the blade is aligned. Consequently, when a sagittal saw is actuated, the blade teeth move in a back-and-forth pattern against the hard tissue or bone to which the teeth are applied. As a consequence of this motion and the forward pressure applied by the surgeon holding the saw, the teeth cut and separate the hard tissue or bone.

A sagittal saw is often used in an orthopedic surgical procedure to selectively remove bone. One particular type of orthopedic surgical procedure in which the saw is used is a joint replacement procedure. As the name implies, in this type of procedure, the surgeon resects the bone between the joints in the patient and substitutes an artificial joint.

In orthopedic surgical procedures, it is very important to ensure that, when a bone section is separated from the rest of the bone, the section is removed along very precise cut lines. This is very important in a joint replacement procedure because the substitute joint typically has a component that is designed to precisely fit in the space defined by cut lines of the section of bone that is left in place.

Therefore, in order to insure that the proper cut lines are formed in the bone, the surgeon typically first mounts a cutting guide, sometimes called a jig, to the bone adjacent to the location where the cut is to be made. One type of cutting guide is in the form of a block formed with a precisely shaped set of slots. The slots define the lines along which the bone is to be cut. The surgeon then performs the surgical procedure by sequentially inserting the saw blade in the slots. Once the blade is inserted in a slot, the saw is actuated. In this manner the surgeon is able to cut the bone along the precisely defined lines along which the bone is to be separated.

Another type of cutting guide is in the form of an open-face block which is mounted to the bone at the appropriate location and defines a guide surface thereon. The surgeon performs the surgical procedure by positioning the saw blade flat against the guide surface to make the desired cut. This type of cutting guide is advantageous in that the visibility of the cutting area is improved from that of cutting guides utilizing slots, since the saw blade is not hidden within the slot.

While presently available sagittal saws and complementary cutting guides work reasonably well, there are some noticeable limitations. As mentioned above, known commercially available sagittal saws are provided with flat planar blades that oscillate. This type of blade invariably rubs against the cutting guide material forming the slot(s) in which the blade is inserted. This repetitive contact wears away this slot-defining material. One problem associated with the wearing away of this material is that it widens the slot. Eventually, the slot may become so wide that it no longer serves to precisely define the cut line it is intended to define. Once a cutting guide is so worn, it needs to be replaced. Moreover, the wearing of the material forming the cutting guide generates a fine dust of the material. This dust inevitably settles on the surgical site at which the procedure is being performed. Consequently, during the procedure, the surgical personnel are required to spend an appreciable amount of time flushing the site to remove this dust. Having to repeatedly perform this process runs counter to one of the primary goals when performing surgery, that one should perform the procedure as quickly as possible to both minimize the likelihood the exposed tissue is open to infection and the amount of time the patient is held under anesthesia.

As discussed above, the oscillating blade of the current surgical saw will repeatedly gall the surfaces of the cutting guide forming the slot in which the blade is inserted. One further disadvantage of this blade galling is that same consumes power, and since many sagittal saws are battery powered, the power expended due to the friction caused by the blade galling reduces the overall amount of power the battery has available to power the saw. In other words, the power consumed to overcome this frictional contact can reduce the overall amount of time the battery, on a single charge, is able to power the saw. Moreover, as a consequence of the saw blade galling against a surface of the cutting guide, and then pulling away from the surface, there is some jerking of the blade. This jerking motion is transferred from the blade through the handpiece into the hand of the surgeon holding the saw. Consequently, the surgeon must exert some muscle control to hold the handpiece steady when he/she is exposed to this jerking motion.

Also, as an inevitable result of the back-and-forth motion of the blade, the surgical saw invariably vibrates. Again, the surgeon is required to engage in some conscious or unconscious physical effort to hold the saw steady when it so vibrates. Over time, having to so hold the saw steady to overcome this vibration can be significantly mentally and physically fatiguing.

Recently, there has been proposed a new type of surgical sagittal saw that does not include a flat oscillating blade. This saw instead includes an endless metal band that is formed with outwardly directed teeth. The band is wrapped around a static guide that extends forward from the handpiece, with the band teeth extending outwardly from the guide. A drive mechanism rotates the band. Since the guide of the proposed saw does not move, it is believed that many of the problems associated with saws that have oscillating blades would be eliminated. One example of this type of saw is disclosed in U.S. Pat. No. 5,725,530.

However, there are disadvantages associated with the above saw. It is expensive to provide the toothed metal band. Also, the metal band appears prone to fatigue and, consequently, breakage. The time it takes to replace this metal band while in the middle of a surgical procedure can appreciably increase the overall time required to perform the procedure.

Moreover, one of the goals of modern surgery is to, whenever possible, perform the procedure using a minimally invasive surgical (MIS) practice. As the name implies, in an MIS procedure only a relatively small incision is made with minimal soft tissue disruption in order to gain access to the surgical site. Minimizing the extent to which a patient's tissue is exposed reduces the amount of tissue that is exposed to the ambient environment and the potential for infection caused by such exposure. Furthermore, reducing the extent to which the patient's tissue is incised minimizes the amount of tissue that then needs to heal.

In order to perform a minimally invasive surgical procedure on a bone or bone joint, only a relatively small portion of the surrounding soft tissue is incised to expose the bone or the joint. Consequently, the bone or joint is not well exposed. In order to make the resection in the bone, the oscillating saw blade that is employed is typically longer than the saw blade used to perform a conventional, resection surgical procedure. Given the relatively long length of the blade, the blade has a mass moment of inertia that is appreciably greater than the mass moment of inertia associated with shorter-length blades. Consequently, when the saw to which this blade is attached is actuated, more vibratory motion is created by the blade and transferred to the rest of the handpiece than when a shorter blade is used. This increased vibratory motion can make it difficult for the surgeon to hold the saw steady. Further, because this longer type of saw blade oscillates along essentially its entire length during the cutting procedure, the saw blade can cause extensive damage to the soft tissue at the incision.

Moreover, a longer blade is more flexible than its shorter counterpart. The added flexibility of the blade can result in the blade making less precise cuts in the bone the blade is used to shape. Unfortunately, it is not possible to reduce this flexibility by simply increasing the overall thickness of the blade. Taking this action increases the mass of the blade and, by extension, the mass moment of inertia of the blade. For the reasons set forth above, increasing the mass moment of inertia of the blade would, in turn, increase the extent to which the associated saw, when actuated, vibrates.

Also, both the sagittal saws that are provided with oscillating blades and the proposed saw with a static guide bar are used with cutting guides that are relatively large in size. The relatively large size of the presently available cutting guides makes it difficult, if not impossible, to perform a minimally invasive surgical procedure.

U.S. Pat. No. 2,854,981 discloses a surgical saw having a saw blade pivotably supported at the end of a beam which extends forwardly from a handpiece. The beam includes a pair of tubes which are secured on opposite sides of a support rod, which tubes house therein reciprocating thrust rods. The thrust rods push against a plate adjacent the blade and cause the blade to undergo pivotal oscillating movement.

This saw, due to the pivotal movement of the blade at the distal end of the saw, would not appear to create excessive vibratory motion and/or soft tissue damage. However, the extension of the saw relative to the cutting slot or kerf created by the blade in the hard tissue or bone is limited. That is, the depth at which the saw can cut is limited to the length of the blade itself, since the beam which supports the blade is much larger than the blade.

Further, the arrangement illustrated in the above patent actuates the blade through compression of the respective thrust rods which then push against the blade to move same. This type of arrangement necessarily requires that the rods be dimensionally large and constructed of a heavy material capable of repeatedly withstanding these types of forces, which then results in a heavy and cumbersome saw.

SUMMARY OF THE INVENTION

This invention is generally related to a new and useful sagittal saw for performing a surgical procedure and a complementary cutting guide for using the saw. The saw of this invention has a static, planar guide bar that extends forward from the saw handpiece. A saw blade is pivotally attached to the distal end section of the guide bar. Drive rods or drive elements are attached to the opposed sides of the blade and are housed within the guide bar. The drive rods are attached to a drive assembly integral with the saw handpiece.

The saw of this invention is used by actuating a motor internal to the handpiece. The drive assembly transfers the power developed by the motor to the drive rods so that the rods simultaneously engage in back-and-forth reciprocating motion in opposite directions. The drive rods, in turn, transfer the reciprocating motion to the saw blade so that the blade teeth move in a back-and-forth or side-to-side oscillating motion.

The pivotal attachment of the saw blade at the distal end of the guide bar results in less vibratory motion of the saw. Further, the static guide bar which supports the blade avoids excessive wearing of the cutting guide, and particularly slotted cutting guides. Of particular advantage is the configuration of the guide bar according to the invention. More specifically, the guide bar is constructed so as to have a relatively small thickness dimension, which in the preferred embodiment is no larger than the thickness dimension of the blade. This allows increased extension or advancement of the blade into the bone, since the guide bar is dimensioned so that same will fit into the cutting slot or kerf created by the blade in the bone. Further, the drive rods are under tension in that same exert a pulling force on the blade to oscillate same. This means that thinner drive rods can be utilized, which results in a lightweight and easy to use saw.

The cutting guide of this invention is defined by a block or body. Pins or other fastening members hold the guide block in a fixed position relative to the bone or other hard tissue to be cut. The cutting guide is formed with one or more outer surfaces that are guide surfaces. The cutting guide is positioned so that the guide surface is in the plane or immediately adjacent the plane in which the cut through the bone is to be made. A capture pin extends upwardly from the guide surface. The guide bar of the saw of this invention is further formed to have an elongated slot. The cutting guide capture pin is seated in the slot to hold the saw guide bar to the cutting guide, and yet allow the saw to both move forward and pivot relative to the cutting guide. The capture pin can be slidably mounted or seated within an elongate slot or track defined in the block which opens through the guide surface, which capture pin is moved by the guide bar of the saw during a cutting procedure to allow lateral movement of the saw across the guide surface. Alternatively, the capture pin can be mounted to the block in a removable manner to allow same to be mounted in multiple locations along the block.

The capture pin reduces the overall size of the cutting guide, which makes it possible to use a cutting guide that is relatively small in size. Further, the cutting guide according to the invention allows greater cutting site visibility of open-face cutting guides as discussed above. However, the capture pin according to the invention avoids the disadvantage of conventional open-face cutting guides wherein the surgeon must make a conscious effort to maintain the saw blade flat against the guide surface of the cutting guide.

BRIEF DESCRIPTION OF THE DRAWINGS

The invention is pointed out with particularity in the claims. The above and further features and advantages are better understood from the Detailed Description below and the accompanying drawings, in which:

Figure 1:
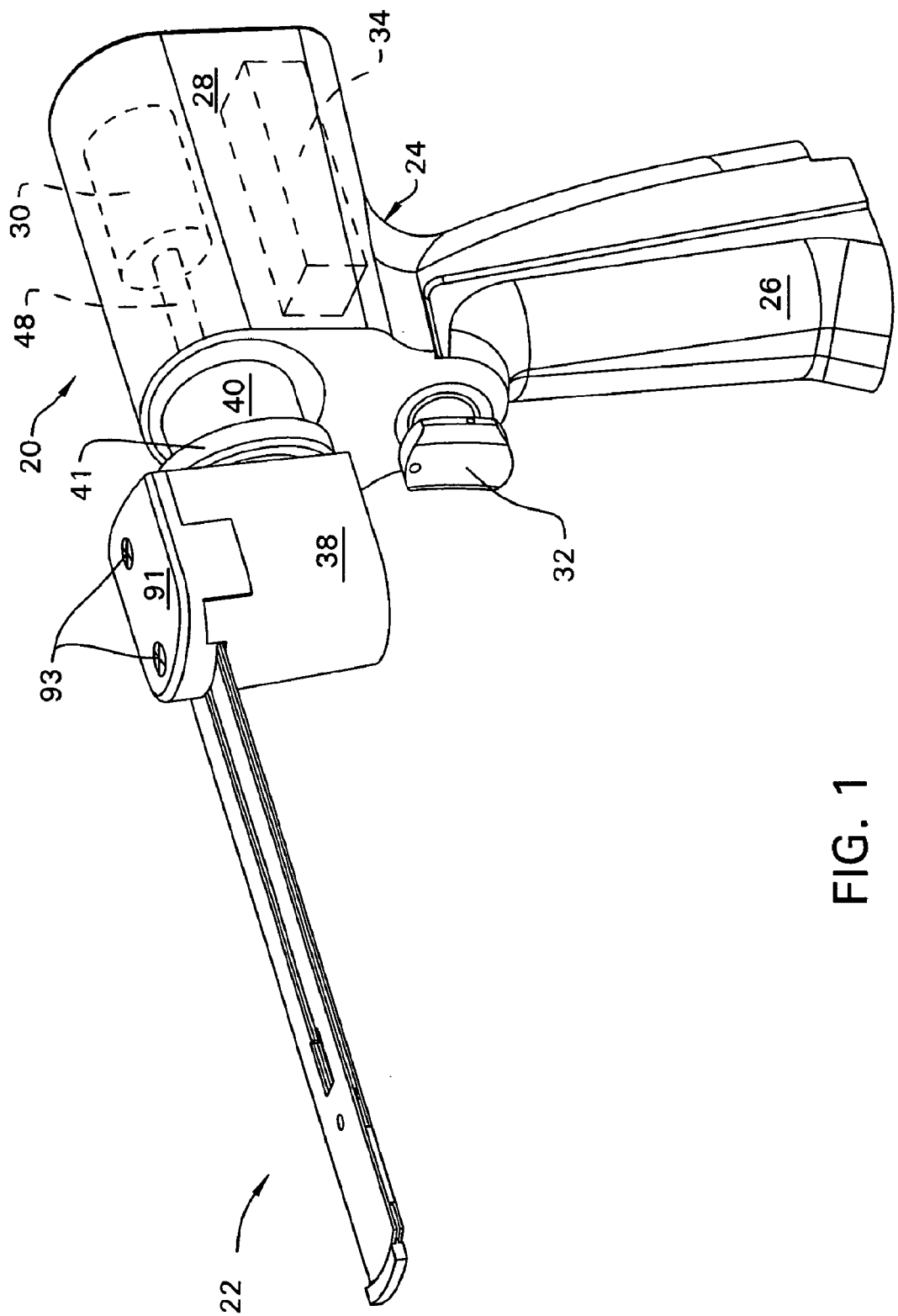
FIG. 1 is a perspective view of the saw and saw blade assembly of this invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement. The word "distally" shall mean directed towards the patient, and the word "proximally" shall mean directed away from the patient. Said terminology will include the words specifically mentioned, derivatives thereof, and words of similar import.

DETAILED DESCRIPTION

FIG. 1 illustrates a surgical saw 20 and complementary blade assembly 22 of this invention. Saw 20 includes a handpiece 24 that functions as the body of the saw. The handpiece 24 is shaped to have a handgrip 26 and an upper shell 28 that extends over the handgrip 26. Internal to the upper shell 28 is a motor 30 (shown in phantom). A battery (not shown) is removably attached to the base of the handgrip 26. A manually retractable trigger 32 extends forward from the distally directed forward surface of the handgrip 26. Located in the upper shell 28 immediately above the trigger 32 and below the motor 30 is a control module 34 (shown in phantom). Electronics integral with the control module 34 monitor the extent to which the trigger is depressed and, based on the trigger state, regulate the actuation of the motor 30.

Located forward from the distally facing front face of the handpiece upper shell 28 is a head 38. Head 38 is the component of the saw 20 to which the blade assembly 22 is attached. The head 38 is attached to the handpiece 24 by a cylindrical neck 40, head 38 and neck 40 being formed as an integral unit. The outer surface of neck 40 is provided with threading (not illustrated). Neck 40 is screw-secured in a forward opening bore in the handpiece upper shell 28 (bore not illustrated).

Figure 2:
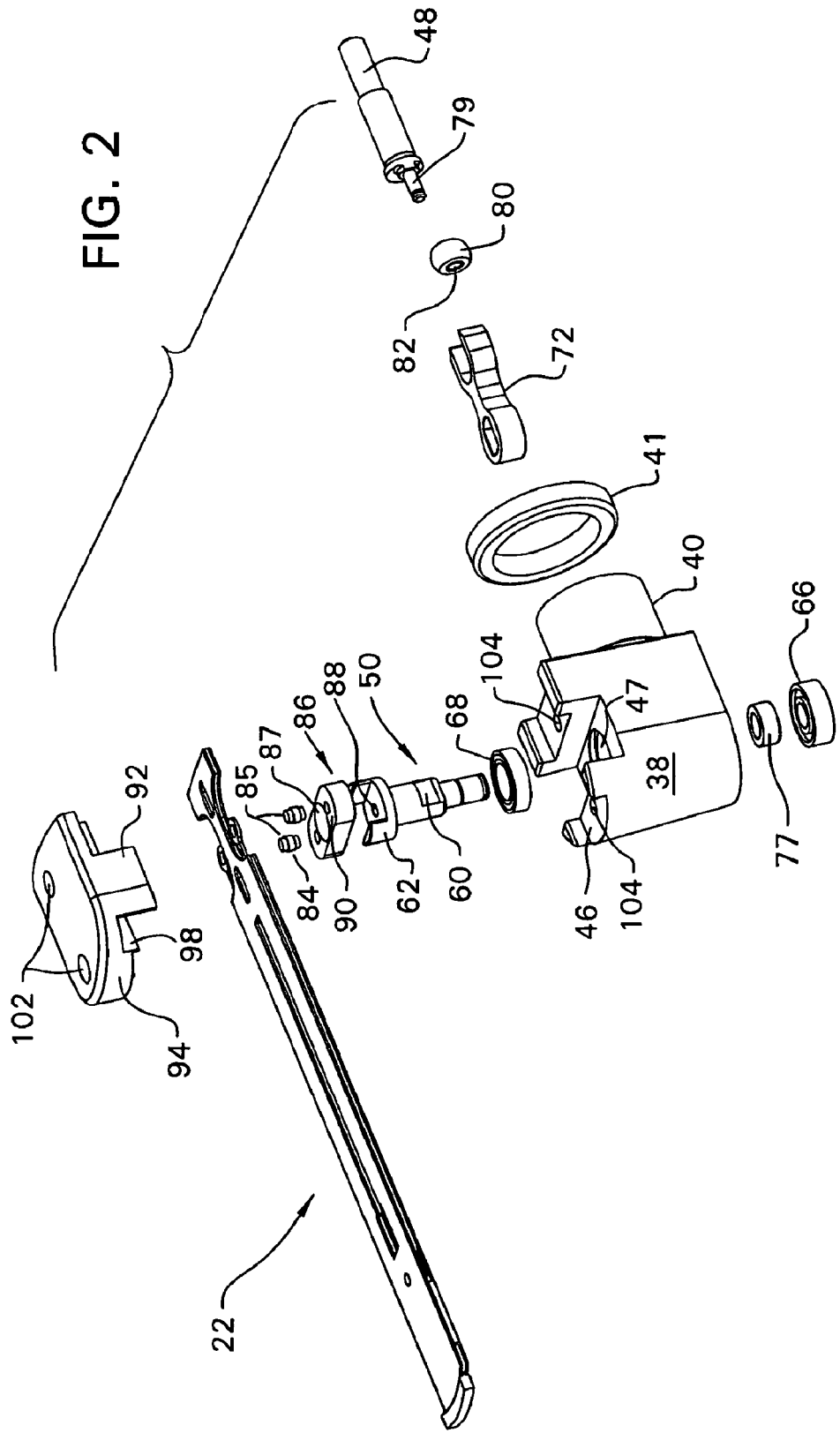
FIG. 2 is an exploded view of the head of the handpiece of this invention.
Figure 3:
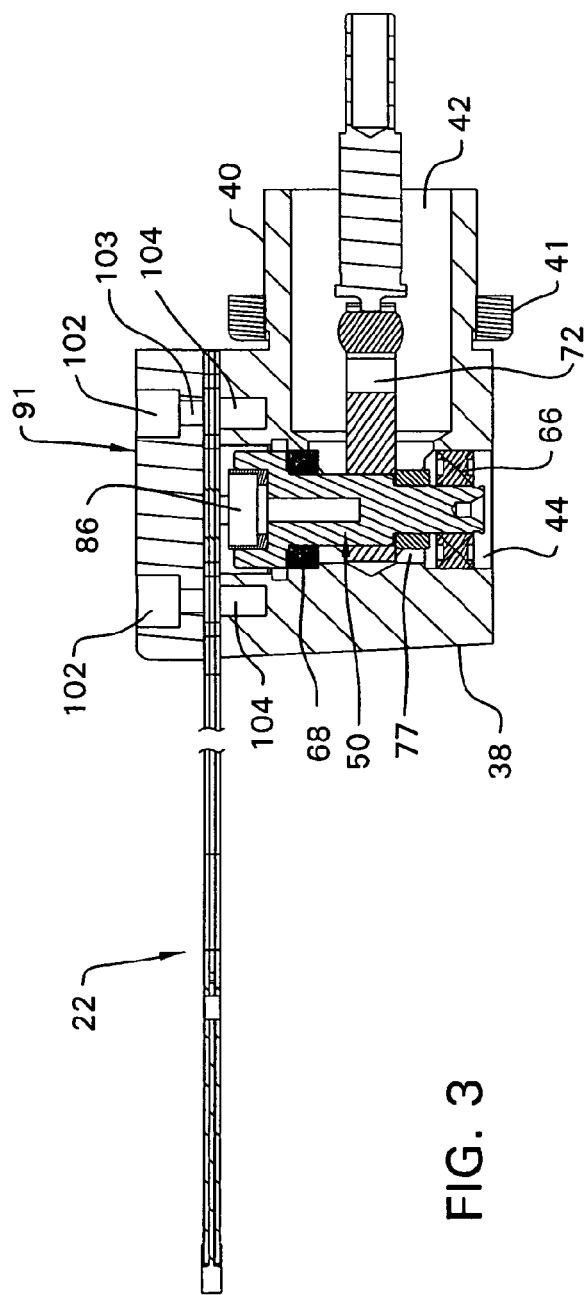
FIG. 3 is a longitudinal cross-sectional view of the head of the handpiece.
Figure 4:
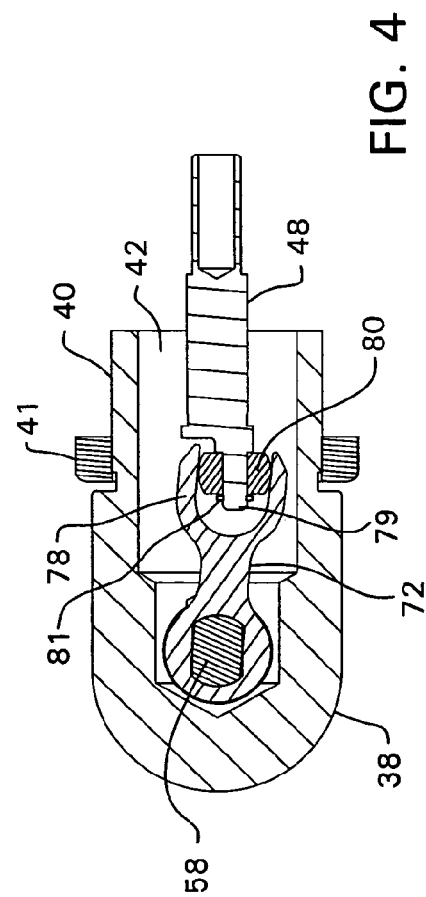
FIG. 4 is a lateral cross-sectional view of the head of the handpiece.

As seen in FIGS. 2-4, a lock ring 41 is threaded over neck 40 and located forward of the upper shell 28. When the handpiece 24 of this invention is assembled, the head 38 and neck 40 are first rotated so as to be in the proper orientation relative to the handpiece upper shell 28. Lock ring 41 is then rotated around the neck 40 so as to press against the front face of the upper shell 28 so as to hold the head 38 and neck 40 in position.

Head 38 is located at the distal end of the neck 40 and has a cross-sectional width greater than the diameter of the neck. The distal facing front face of the head is curved. A bore 42 extends longitudinally through the neck 40. The bore 42 terminates in a bore 44 that extends longitudinally through the head 38. Since the longitudinal axes of head 38 and neck 40 are perpendicularly offset from each other, it should be understood that the axes of bores 42 and 44 are likewise perpendicularly offset.

The top of the head 38 is formed so as to define two grooves 46 and 47, each of which has a rectangularly shaped cross-sectional profile. Groove 46 extends longitudinally along the head 38, from the distal facing front face towards neck 40. Groove 47 extends perpendicular to and crosses groove 46. Groove 47 is deeper than groove 46 such that groove 47 bisects groove 46. Bore 44 opens into the top surface of the head 38 that defines groove 47.

Internal to head 38 and neck 40 is a drive assembly that actuates the actual saw blade of saw blade assembly 22 that is now described by reference to FIGS. 2 and 3. The drive assembly includes a drive shaft 48 that extends from the handpiece upper shell 28 into the neck 40. In some versions of the invention, drive shaft 48 may be the actual output drive shaft of motor 30. In some versions of the invention, drive shaft 48 may be an output drive shaft of a speed reduction gear assembly or an idler shaft to which the actual motor drive shaft is connected.

Figure 5:
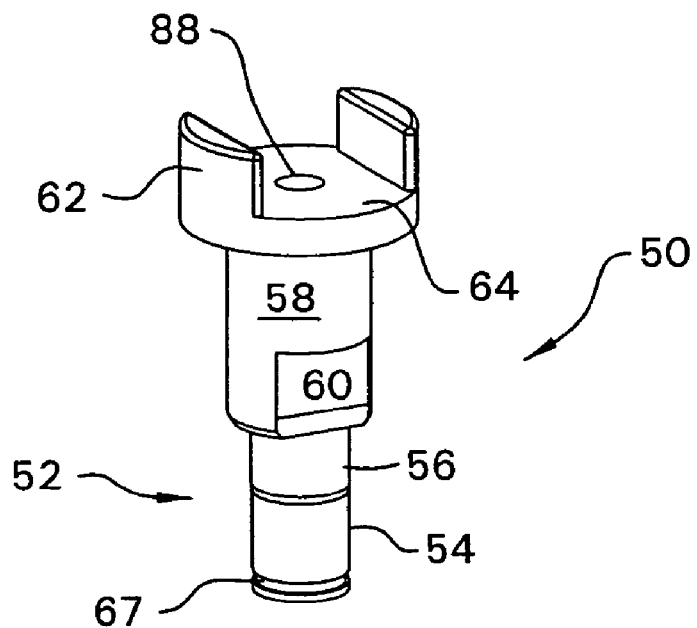
FIG. 5 is a perspective view of the drive base.

The rotation of the drive shaft 48 oscillates, via a drive link 72, a generally cylindrical, multi-section head drive shaft or drive base 50 that is rotatably mounted in head bore 44. The head drive shaft 50, now described with reference to FIG. 5, is shaped to have a cylindrical stem 52. Stem 52 has a first lower section 54 with a first outer diameter and a second upper section 56 with a second outer diameter that is slightly larger than the first diameter. Above the stem second section 56, head drive shaft 50 has a main section 58 with an outer diameter greater than that of either of the stem sections 54 and 56. Generally, the main section 58 is cylindrical. However, the main section 58 is formed so that the lower section thereof has two diametrically opposed flats 60. Above the main section 58, head drive shaft 50 is formed to have a head 62. The head 62 is generally circular in shape and has an outer diameter greater than that of the underlying main section 58. Head 62 is further formed to have a slot 64 that extends along the length of the head. The longitudinal axis of slot 64 is perpendicular to the planes in which flats 60 lie.

When the handpiece 26 is assembled, most of the head drive shaft 50 is disposed in head bore 44. The upper portion of the head 62 extends into the bottom portion of the head groove 47.

Bearing assemblies 66 and 68 rotatably hold head drive shaft 50 in head 38. Bearing assembly 66 extends between the stem lower section 54 and the adjacent inner wall of head 38 that defines bore 44. The inner race of bearing assembly 66 abuts the step between the lower and upper sections 54 and 56, respectively, of the stem 52. A retaining ring (not illustrated) snap fitted into a groove 67 formed in the end of the stem lower section 54 holds the bearing assembly 66 to the stem 52.

Bearing assembly 68 is located around the main section 58 immediately below the head 62. Bearing assembly 68 thus extends between the main section 58 and the inner wall of the head that defines bore 44. In the depicted version of the invention the head is shaped so that the bore 44 has a large diameter counterbore (not identified). The outer race of bearing assembly 68 seats against the stepped surface between the counterbore and main sections of bore 44.

Figure 6:
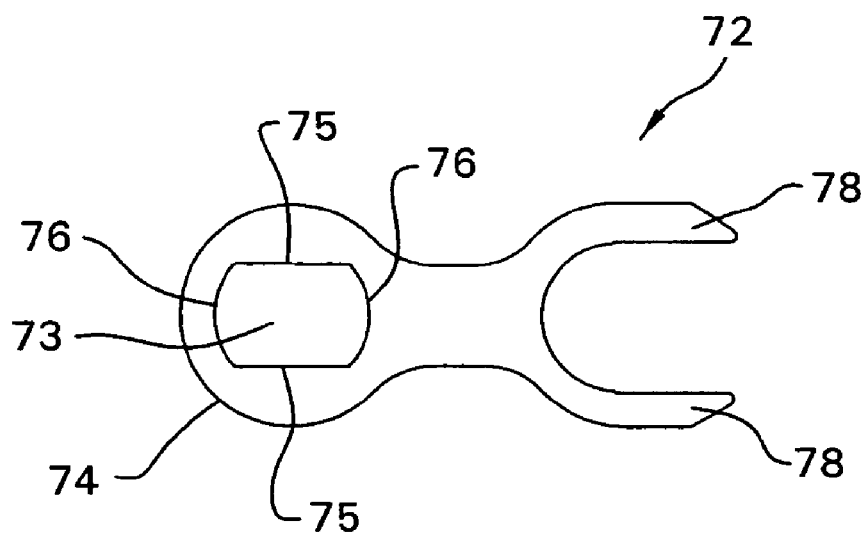
FIG. 6 is a plan view of the drive link.

Drive link 72, as best seen in FIG. 6, has a circular distal end 74 formed with a closed opening 73. Opening 73 is defined by two opposed flat walls 75 and two opposed curved walls 76. More particularly, the drive link 72 is shaped so that, when the drive link is fitted to the head drive shaft 50, the flat walls 75 and curved walls 76 that define the opening 73 closely abut, respectively, the flats 60 and adjacent curved surfaces of the main section 58 of head drive shaft 50.

A collar 77 is press-fit to the stem upper section 56. Collar 77 prevents downward slippage of the drive link 72 from the main section 58.

Extending proximally from the distal end that defines opening 73, drive link 72 is shaped so as to have a proximal end that has two parallel opposed tines 78. Tines 78 are generally directed towards drive shaft 48.

Drive shaft 48 is formed to have a cylindrically-shaped cam 79 that extends forward from the front end of the drive shaft. Cam 79, it will be observed, is parallel to and axially offset from the longitudinal axis of drive shaft 48. The drive link 72 is positioned relative to the drive shaft so that cam 79 is disposed between the drive link tines 78.

A spherical bearing 80 is fitted over cam 79. The drive shaft cam 79 extends into an opening 82 in the center of the spherical bearing 80. A snap ring 81 holds bearing 80 to the cam 79. Bearing 80 is positioned and dimensioned to be closely slip fitted between the drive link tines 78. Thus, bearing 80 transfers the rotational movement of cam 79 around the center axis of the drive shaft 48 to the drive link 72 as an oscillatory movement, and the drive link 72 transfers this oscillatory movement to head drive shaft 50.

An oscillating bar 86 is secured in the slot 64 formed in the drive base head 62. More specifically, a threaded fastener (not illustrated) that extends through an opening 87 formed in the oscillating bar 86 and a bore 88 in the head drive shaft 50 that opens into slot 64, holds the bar 86 to the head drive shaft 50. Oscillating bar 86, it will be understood is positioned in the base of the head groove 47. Collectively, the assembly that oscillates bar 86 and the bar 86 are constructed so that, when the bar oscillates, the component does not contact the opposed interior walls of head 38 that define head groove 47.

Two pins 85 are press-fit into separate openings 90 formed in the top of oscillating bar 86. Openings 90 are centered on the longitudinal axis of the oscillating bar 86 and symmetrically located around opening 87. Each pin 85 has a relatively wide center waist section 84. The presence of the waist sections 84 limit the extent to which the pins 85 are press-fit into the oscillating bar 86.

A cover 91 is secured over the top of the saw head 38 so as to cover the proximal end of the saw blade assembly 22, i.e. the end secured to the head 38. Cover 91 is shaped so as to have legs 92 that extend downwardly from opposed sides of the cover (one leg shown). The legs 92 seat in opposite ends of head groove 47.

Cover 91 is further formed to have a downwardly extending center rib 94 that extends the length of the cover. Rib 94 is spaced inwardly from legs 92. When the saw 20 and complementary blade assembly 22 of this invention are assembled together, the proximal end of the blade assembly 22 is seated in head groove 46. Rib 94 seats in head groove 46 above the proximal end of the blade assembly 22. The rib 94 is formed with two parallel opposed flanges 98 (one flange shown). Flanges 98, which are located on opposed sides of the rib 94, extend the length of the rib. When the saw 20 and blade assembly 22 are assembled together, each flange 98 is located between a side edge surface of the blade assembly 22 and the adjacent inner wall of the head 38 that defines groove 46.

Threaded fasteners 93 removably secure the cover 91 to the head 38. Each fastener 93 extends through an opening 102 formed with a counterbore 103 (FIG. 3) that extends through the cover 91 and rib 94 into a complementary threaded bore 104 formed in the head 38. Bores 104, it will be observed extend downwardly from the base of head groove 46.

As seen by reference to FIGS. 1, 7, 7A and 8, the saw blade assembly 22 includes a guide bar assembly 110 that extends distally forward from handpiece head 38. A saw blade 112 that is pivotally connected to the guide bar assembly 110 extends forward from the distal end of the guide bar assembly. Thin, plate-like drive rods or drive elements 114 extend between the oscillating bar 86 located in the head 38 of handpiece 24 and the saw blade 112. The drive rods 114 transfer the oscillating motion of bar 86 to the saw blade 112 so that when the saw 20 is actuated, the saw blade 112 moves in a back-and-forth motion.

The guide bar assembly 110 consists of three planar, plate-shaped bars, i.e. a bottom bar 116, an inner bar 118 and an outer bar 120 that are stacked together. Bottom bar 116 and outer bar 120 are generally identical in overall length and width. The bottom bar and outer bar 116 and 120, respectively, are each formed so that immediately forward of the proximal end, there are two inwardly directed cutouts 122. The most distal front ends of both the bottom bar 116 and outer bar 120 are curved (curved distal ends not identified). The bottom bar 116 is further formed to define opposed rectangular notches 124 that are located proximally of the front end and extend inwardly from the opposed sides of the bar.

Inner bar 118 is shorter in overall length and narrower in overall width than the bottom bar and outer bar 116 and 120, respectively. Inner bar 118 is formed to have a proximal end stem 128 with a proximal end edge that is aligned with the proximal end edges of the surrounding bottom bar 116 and outer bar 120. A short distance forward from the proximal end edge, the inner bar stem 128 curves inwardly so as to have a curvature that is aligned with the adjacent inwardly curved side edges of the bottom bar 116 and outer bar 120. Forward of where the inner bar 118 curves inwardly, the bar 118 has a constant width.

Inner bar 118 has an overall length that is typically from 70 to 90% of the overall length of the bottom and outer bars 116 and 120, respectively. In more preferred versions of the invention, the overall length of the inner bar 118 is between 75 and 85% of the overall length of the bottom and outer bars 116 and 120, respectively. Forward of stem 128, inner bar 118 has a width that is typically between 30 and 95% of the width of the bottom and inner bars 116 and 120, respectively. In more preferred versions of the invention, the width of the main portion of the inner bar 118 is between 50 and 90% of the width of the surrounding sections of the bottom and outer bars 116 and 120, respectively.

The guide bar assembly 110 is assembled by first welding a pair of support bars 130 in notches 124 of the bottom bar 116. The support bars 130 are generally rectangular in shape. One support bar 130 is welded in each notch so as to extend upwardly from the bottom bar 116.

The inner bar 118 and outer bar 120 are then stacked over the bottom bar. The support bars 130 are welded to the abutting inwardly directed face of the outer bar 120. Once the guide bar assembly 110 is partially assembled (i.e. the inner bar 118 is still loose at this point), the sandwiched metal forming the bottom, inner and outer bars 116, 118 and 120, respectively, is selectively removed in a single operation to form a generally rectangular guide slot 132 and two oval shaped openings 134 and 136. Slot 132 and openings 134 and 136 are longitudinally aligned along the center longitudinal axis of the bars 116, 118 and 120. Slot 132 is located in the portion of the guide bar assembly that extends forward from saw head 38. The guide bar assembly is further formed so as to define an opening 133 that is contiguous with and communicates with the distal end of slot 132. Opening 133 is wider than slot 132. Openings 134 and 136 are formed in the portions of the guide bar assembly 110 that seat in the base of head groove 46. Opening 136 is the more proximally located of the two openings. Portions of the edge surfaces of the bottom, inner and outer bars 116, 118 and 120 that define slot 132 and openings 133, 134 and 136 are then welded together so as to secure the bars to each other.

When the blade assembly 22 is attached to saw 20, guide bar openings 134 and 136 are each in registration with one of the cover openings 102 and complementary head openings 104. Thus, openings 134 and 136 each accommodate a separate one of the fasteners 93 that secure the cover 91 to the head 38. Fasteners 93 likewise hold the saw blade assembly 22 to the saw 20. Openings 134 and 136 are oval to accommodate for manufacturing variations between the components of this invention. The purpose of the guide slot 132 and companion opening 133 is explained hereinafter.

It will be appreciated that blade assembly 22 may alternatively be secured to saw 20 without the use of fasteners 93. For example, blade assembly 22 can be fastened to saw 20 by a detent or other capture arrangement which would allow the proximal end of blade assembly 22 to be quickly fastened to saw 20.

Guide bar assembly 110 also has a pivot pin 140 formed of hardened metal, such as tungsten carbide. Pivot pin 140 is located immediately forward of the distal end of the inner bar 118 and extends between the bottom and outer bars 116 and 120, respectively. More particularly, the bottom bar 116 and outer bar 120 are formed with holes 142 and 144, respectively. The opposed ends of the pivot pin 140 are welded or otherwise secured in holes 142 and 144.

From the foregoing description, it should be understood that the inner bar 118 and support bars 130 hold bottom bar 116 and outer bar 120 apart or in spaced relation from each other. Inner bar 118 and the support bars 130 also contribute to the overall rigidity of the guide bar assembly 110.

Figure 9:
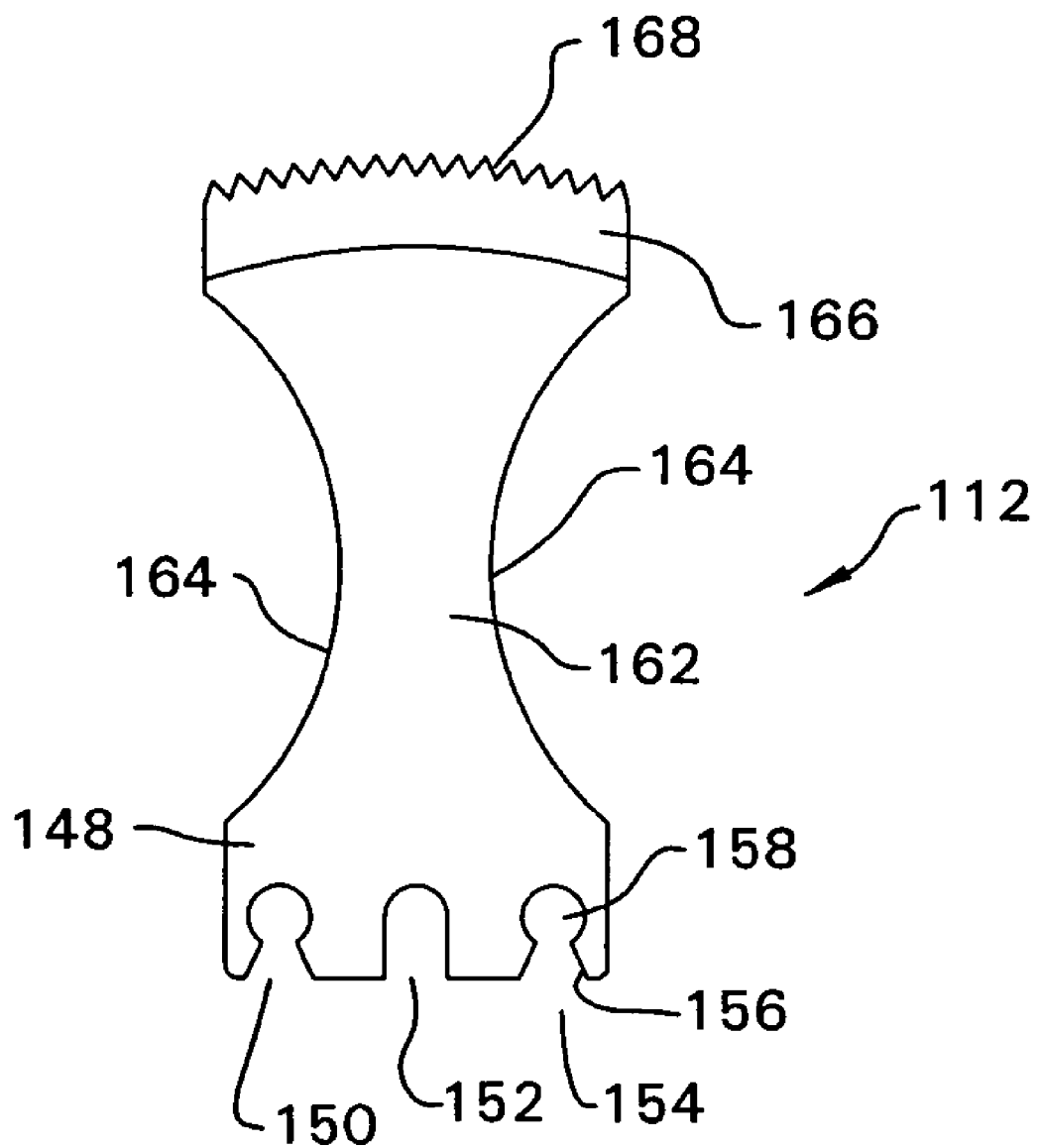
FIG. 9 is a plan view of the saw blade.

The saw blade 112 is now initially described in detail by reference to FIG. 9. The saw blade 112 is a single monolithic piece of flat-shaped metal, such as 420 stainless steel. The saw blade 112 is shaped to have a generally rectangular base 148 that forms the proximal end of the blade 112. Base 148 is shaped to have three notches 150, 152 and 154 that extend forward from the proximal end of the base 112. Notch 152, the middle one of the three notches, is U-shaped and is located along the longitudinal center axis of the saw blade 112.

Notches 150 and 154 are located on opposed sides of notch 152 and are equidistantly spaced from the longitudinal center axis of the saw blade 112. Notches 150 and 154 are identically shaped. Specifically, the saw blade 112 is shaped so that each notch 150 and 154 has a tapered proximal section 156. Specifically, the notch proximal sections are tapered such that the sections have the greatest width adjacent the proximal edge of the saw blade 112. Integral with and located forward of the proximal section 156, each notch 150 and 152 has a distal section 158 with a circular cross-sectional profile. The diameter of the notch distal sections 158 is approximately equal to that of the widest width of the proximal sections 156.

Extending forwardly from the base 148, saw blade 112 has a main section 162. In the illustrated embodiment, the main section is formed to have two opposed sides 164 that have a concave curvature. Owing to the curvature of sides 164, the narrowest width portion of the saw blade main section 162 is the middle portion of the main section.

Forward of the main section, saw blade 112 in the illustrated embodiment has an arcuately shaped head 166. It will be appreciated that blade 112 need not be outwardly curved as shown, and instead may have other configurations. Head 166 is formed with teeth 168. The head 166 is the actual cutting portion of the saw blade 112. For the reasons discussed below, the blade 112 is formed so that head 166 has a thickness greater than that of the base 148 and main section 162.

It is anticipated that saw blade 112 will typically have a side-to-side width of about 1.5 inches or less and often about 0.9 inches or less. The overall length of the saw blade 112 from the proximal end of the base 148 to the most distal tooth 168 will be about 3.0 inches or less and often about 1.5 inches or less.

Figure 7:
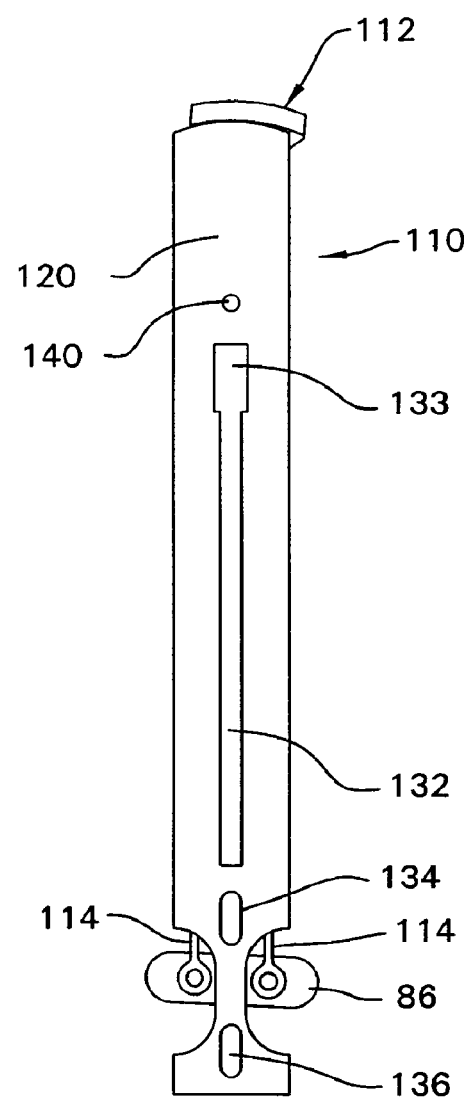
FIG. 7 is a plan view of the saw blade assembly of this invention.
Figure 7A:
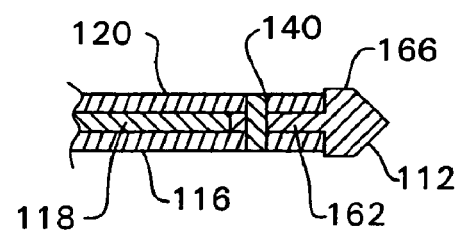
FIG. 7A is a cross-sectional view of the distal end of the saw blade assembly of FIG. 7 along the longitudinal center axis of the saw blade assembly.
Figure 8:
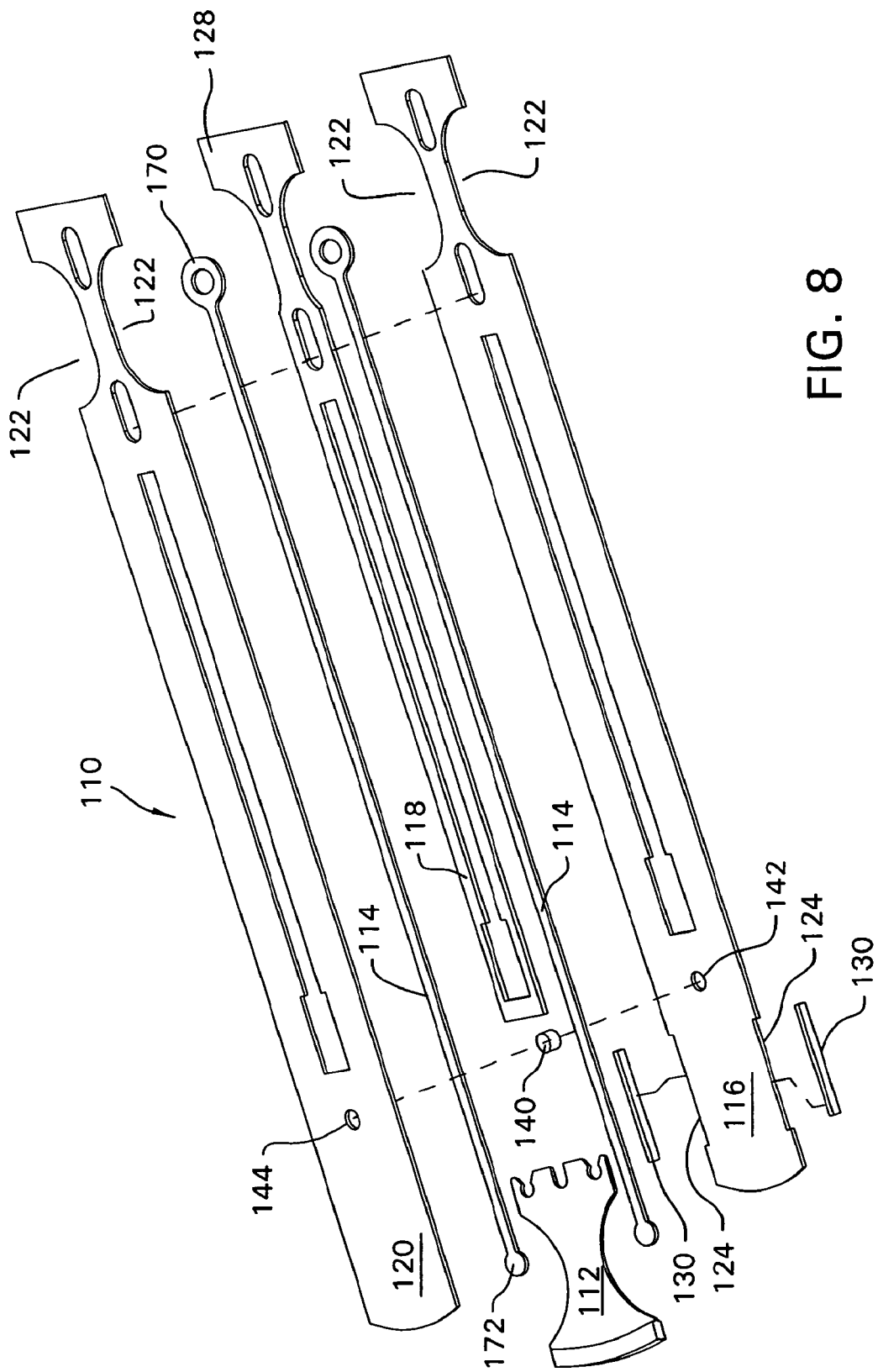
FIG. 8 is an exploded view of the saw blade assembly.

Collectively, the saw blade assembly 22 is constructed so that the blade head 166 has a depth, i.e. a thickness, greater than that of the adjacent guide bar assembly 110 as shown in FIG. 7A. The saw blade 112 is shaped so that the opposed top and bottom surfaces of the blade head 166 extend, respectively, above and below the adjacent top and bottom surfaces of the guide bar assembly 110. As a result of this design, when saw 20 is actuated and the blade head 166 pressed into the bone, the resultant kerf is slightly larger than the thickness of the guide bar assembly 110. This facilitates the movement of the guide bar assembly 110 through the kerf as the bone is cut. In practice, it is anticipated the saw blade assembly 22 will be designed so the blade head 166 has a thickness that is approximately 0.010 inches greater than that of the guide bar assembly 110 from which the head extends. The saw blade 112 is shaped so that the extra thickness of the head 166 is symmetrically arranged relative to the top and bottom surfaces of the guide bar assembly 110. Thus, the blade head 166 typically extends approximately 0.005 inches beyond each of the top and bottom surfaces of the guide bar assembly.

In saws of this invention with saw blade assemblies 22 designed for use in orthopedic surgery, the guide bar assembly will often have a thickness of approximately 0.090 inches. The complementary saw blade head 166 will therefore have a thickness of approximately 0.100 inches. It is anticipated that the thinnest saw blade assemblies 22 designed for orthopedic surgery will have guide bar assemblies with a thickness of 0.040 inches and blade heads with thicknesses of 0.050 inches. These thin saw blade assemblies would be designed for use with conventional cutting guides that are formed with narrow guide slots.

The saw blade 112 is disposed between the distal end sections of the bottom and outer bars 116 and 120, respectively. The saw blade 112 is positioned between bars 116 and 120 so that the pivot pin 140 seats in notch 152. Saw blade 112 thus pivots around pin 140.

The drive rods 114 connect the saw blade 112 to the opposed ends of the oscillating bar 86. The drive rods 114 are formed of a metal such as 17-4 stainless steel. This material has a slight degree of elasticity for purposes that will be clear from the following description. As seen by reference to FIG. 8, the proximal end of each drive rod 114 is formed to have a ring 170. The distal end of each drive rod 114 is formed to have a solid, circularly shaped head 172.

When saw 20 and blade assembly 22 of this invention are assembled together, each drive rod 114 is located between the bottom and outer bars 116 and 120, respectively and adjacent one side of the inner bar 118. The proximal end ring 170 of each drive rod is fitted over a separate one of the pins 85 integral with the oscillating bar 86. The distal end head 172 is seated in the distal section 158 of the adjacent saw blade notch 150 or 154.

In practice, in the described version of the invention, a saw blade 112 is removed and replaced by first removing cover 91 from head 38. The saw blade assembly 22 is then removed from the head 38 so that the drive rod rings 170 are lifted off the pins 85. Once the guide bar assembly 110 is free of the head, the saw blade 112 is pulled forward so as to expose the drive rod heads 172. Once the saw blade 112 is so positioned, it is a simple matter to remove the blade from the drive rods 114, fit a new blade to the drive rods and push the blade and drive rods proximally back towards the saw head 38 to a position where notch 152 engages the pin 140. The reassembled saw blade assembly is then reattached to the saw head 38.

Figure 10:
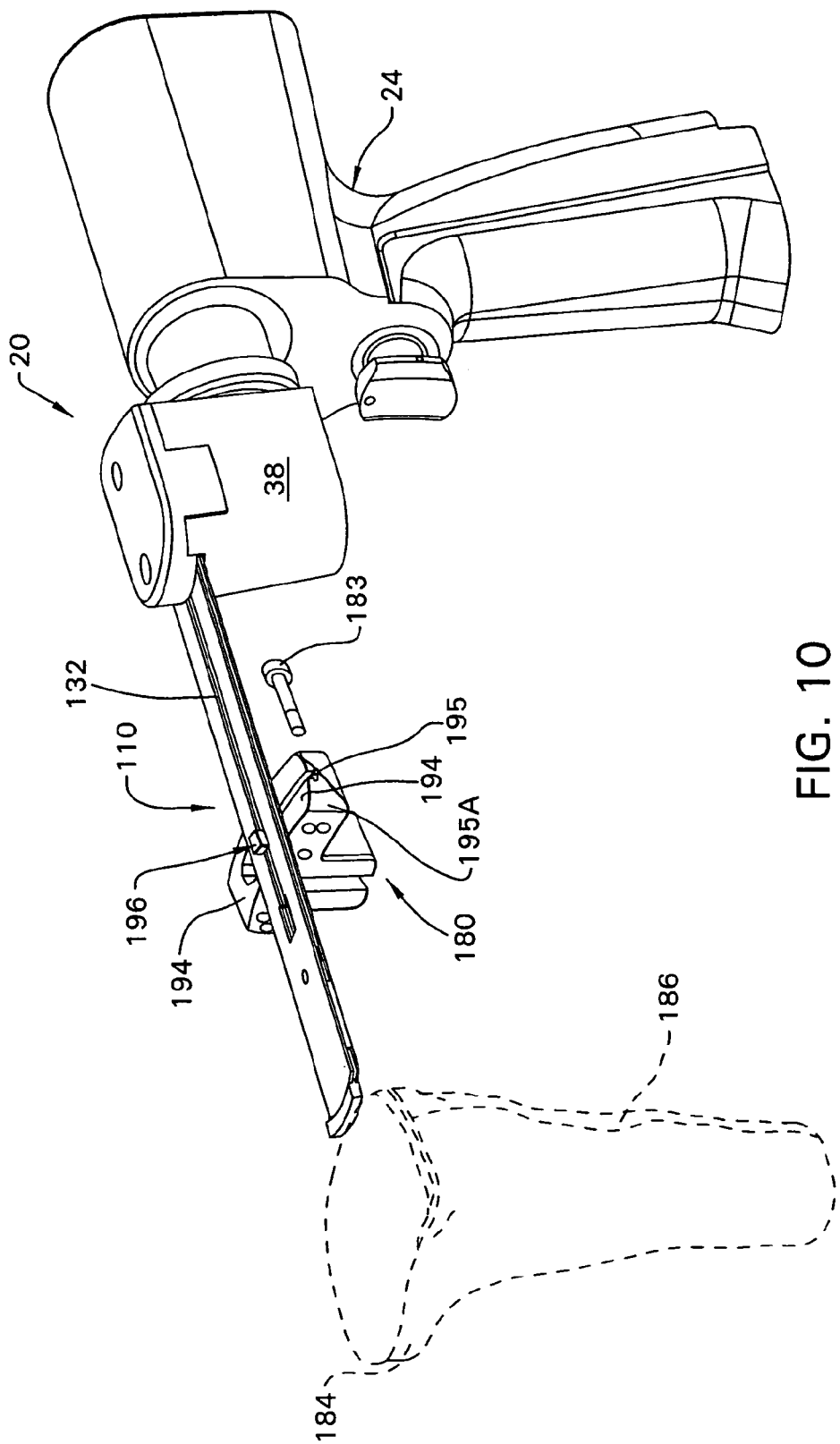
FIG. 10 is a perspective view of how the saw and cutting guide of this invention are collectively used to make a defined cut in a section of body tissue, the body tissue being a diagrammatic representation of a portion of bone.
Figure 11:
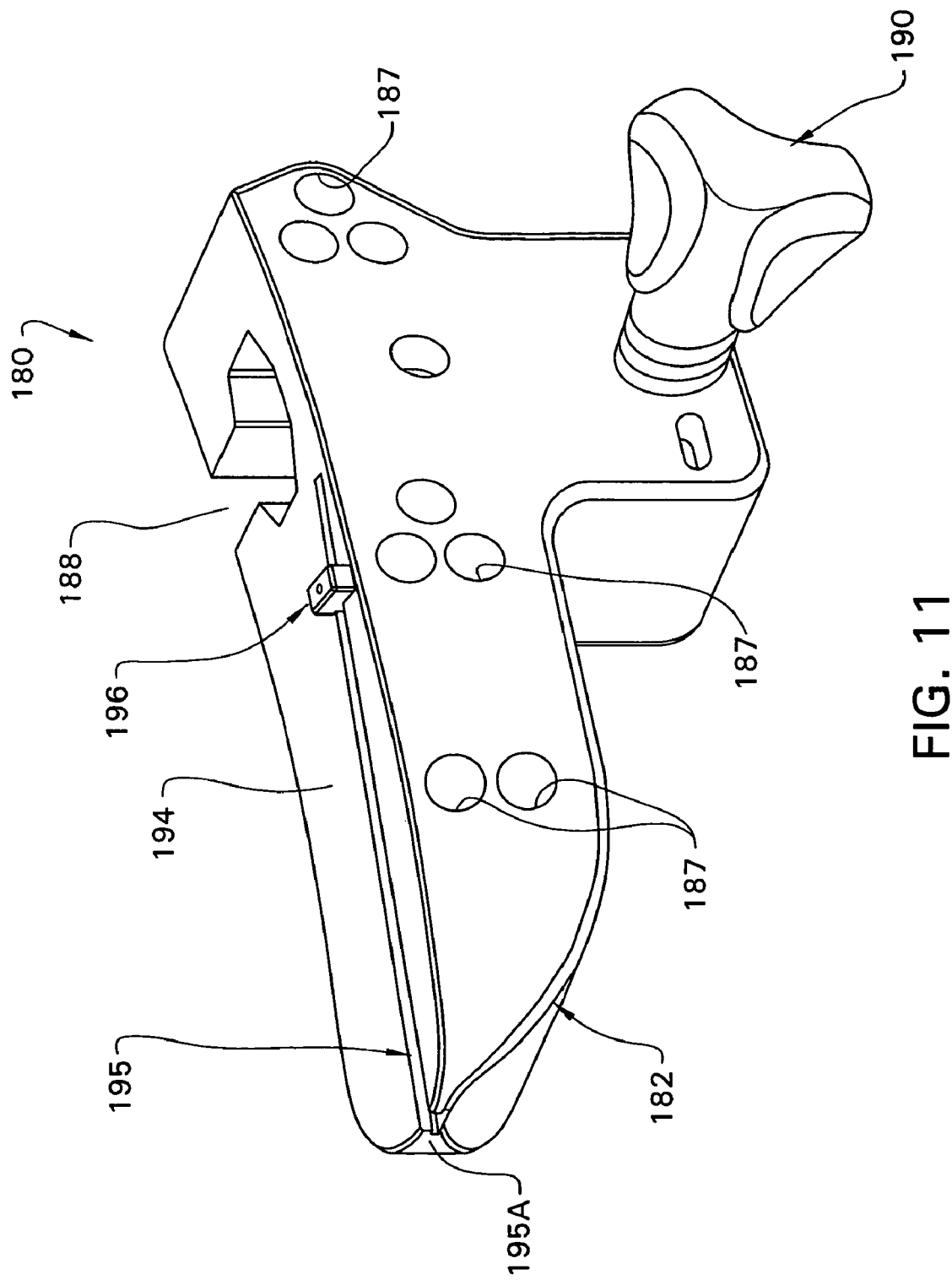
FIG. 11 is a perspective view of the cutting guide of this invention.

FIG. 10 illustrates how a cutting guide 180 of this invention is used to hold the saw 20 and saw blade assembly 22 steady so as to facilitate the making of a desired cut in the bone to which the saw blade 112 is applied. FIG. 11 shows the cutting guide in an isolated view. Cutting guide 180, sometimes referred to as a jig, includes a block or body 182 which can be affixed to most bone joint resection surfaces. In the depicted version of the invention, block 182 is generally L-shaped though this need not always be the case. In practice, cutting guide 180 is temporarily fitted to the proximal portion or head 184 of a tibia 186 (tibia represented diagrammatically). The cutting guide 180 is positioned so that the long side of the block extends perpendicularly across the proximal portion 184. In FIG. 10, cutting guide 180 is shown spaced rearwardly from head 184 for illustrative purposes. Pins 183 (one shown) temporarily secure block 182 to the tibia 186. The pins 183 extend into the tibia 186 through bores 187 formed in the block 182.

Block 182 in the illustrated embodiment defines therein a groove 188, although this need not always be the case. Groove 188 (FIG. 11) extends vertically through the long-width end section of the block 182. Thus, groove 188 is generally parallel to tibia 186 and extends inwardly from the surface of the block 182 positioned adjacent the tibia 184. Groove 188 is shaped to receive an alignment rod used to facilitate the positioning of cutting guide 180. (The alignment rod is not part of this invention.) A thumb screw 190, the head of which is shown in FIG. 11, is mounted to the proximal portion of the block 182 located below the long upper section thereof. The thumb screw 190 projects into groove 188 to facilitate the temporary securing of the cutting guide 180 to the alignment rod.

The topmost outer surface of block 182, the surface depicted as extending perpendicularly relative to the tibia portion 184, is referred to as the guide surface 194. The guide surface 194 is in a plane that intersects the tibia, in the illustrated example, the tibia portion 184.

Figure 11A:
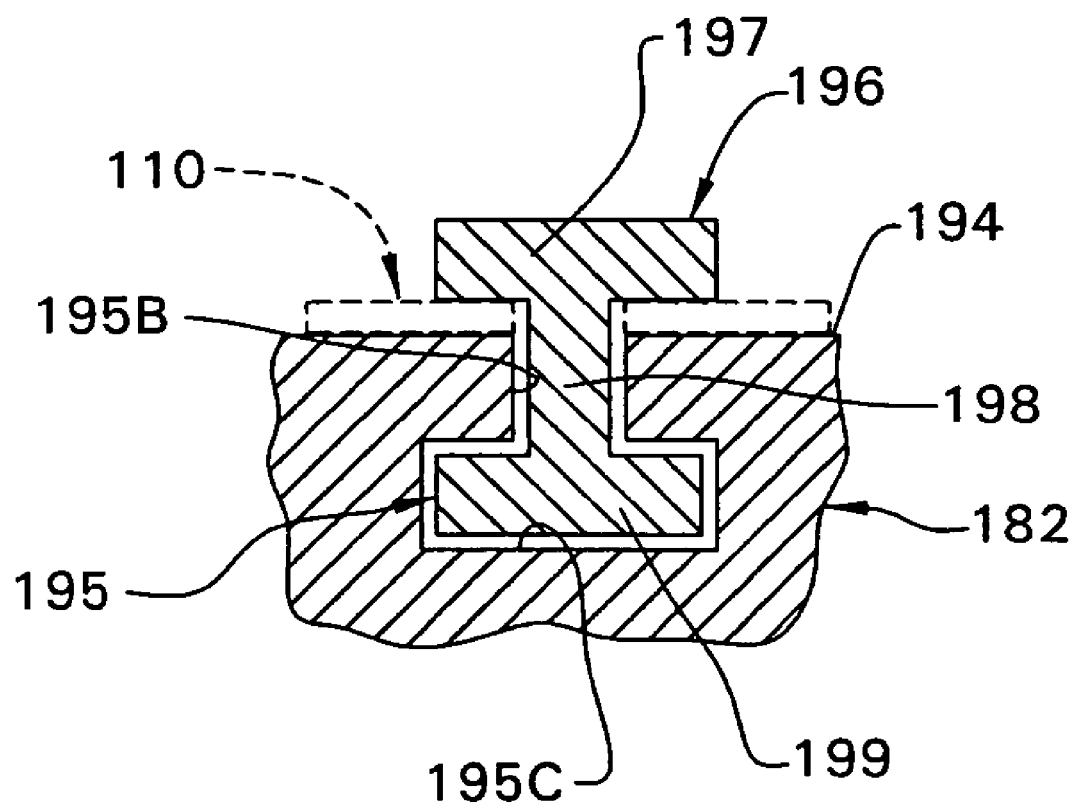
FIG. 11A is an enlarged cross-sectional view of the cutting guide shown in FIG. 11.

The block 182 defines therein an elongated slot, channel or track 195 which opens upwardly through guide surface 194 and extends across a substantial portion of the long upper portion of block 182. In the illustrated embodiment, the track 195 at one end opens sidewardly through a terminal side surface 195A of block 182 and terminates at an opposite closed end adjacent groove 188. With reference to FIG. 11A, track 195 is defined by an upper portion 195B which opens upwardly through guide surface 194 and a lower portion 195C which opens into or communicates with upper portion 195B. Lower portion 195C has a greater width than upper portion 195B to provide track 195 with an inverted T-shaped or dovetail configuration.

As shown in FIGS. 10-11A, a capture pin or capture element 196 is movably and slidably mounted within track 195 of block 182. Capture pin 196 has an upper enlarged part or head 197 which is located above guide surface 194, a stem or middle section 198 which is connected to and projects downwardly from head 197, and a lower part or base 199 which is connected to and projects downwardly from stem 198. The width diminsions of stem 198 and base 199 are slightly less than the respective width dimensions of upper and lower portions 195B and 195C, respectively, to allow sliding movement of capture pin 196 within track 195. Further, the stem 198 of pin 196 is sized so that same can travel within guide slot 132 of guide bar assembly 110, and head 197 is sized to have a greater width than guide slot 132. When the capture pin 196 is positioned within track 195, the head 197 is spaced upwardly a short distance from guide surface 194 as shown in FIG. 11A to allow positioning of guide bar assembly 110 between head 197 and guide surface 194 as shown in dotted lines and as discussed further below. The space defined between the lower surface of head 197 and guide surface 194 is large enough to allow movement of guide bar assembly 110 relative to cutting guide 180.

The saw 20 including saw blade assembly 22 and cutting guide 180 are used by first affixing the cutting guide 180 to the bone to be cut with pins 183. More particularly, the cutting guide 180 is secured to the bone so that the guide surface 194 is immediately below the plane of the bone along which the cut is to be made. The saw 20 is then fitted to the cutting guide 180. This is accomplished by passing the capture pin head 197 through the wide diameter opening 133 of the guide bar assembly 110. The saw is then moved forward so that stem 198 seats in the guide bar assembly slot 132 so as to hold the guide bar assembly, as well as the attached saw 20, to the cutting guide 180. The surgeon then makes the desired cut by depressing the trigger 32 so as to actuate the motor 30. The actuation of the motor 30 results in the oscillation of bar 86. The movement of bar 86 is transferred by drive rods 114 to the saw blade 112 so as to cause a back-and-forth movement of the blade 112 across the distal end of the guide bar assembly 110 and about pivot pin 140. The surgeon then presses the saw into the bone, tibia portion 184. The cut is made along the desired line by moving the saw so that the guide bar assembly 110 pivots around stem 198 of capture pin 196. The saw can be pushed forward so that blade 112 cuts completely through the bone. During the procedure, the guide bar assembly 110 is constrained between the guide surface 194 and the head 197 to ensure that as the blade 112 is pressed forward into or towards the bone, the cut in the bone is made in the desired cut plane as determined by guide surface 194. Further, during the cutting process, the capture pin 196 is moved by the guide bar assembly 110 within and along track 195 to allow lateral movement of the saw 20.

After the desired cut is made, the saw is retracted so that guide bar opening 133 is again in registration with the capture pin head 197. The saw is then lifted free of the cutting guide 180 and the cutting guide 180 released from the bone.

The saw 20 and saw blade assembly 22 are thus constructed so that the only exposed component that moves side-to-side is the saw blade head 166, the most distal component of the saw. The guide bar assembly 110 remains static with respect to the rest of the saw 20. Thus, when the saw of this invention is inserted in a conventional cutting guide formed with a guide slot, once the saw blade starts cutting through bone, the only saw component that abuts the surfaces forming the guide slot are the surfaces of the guide bar assembly 110. Since the guide bar assembly is relatively static, this abutment does not excessively wear the material defining the slot in the cutting guide. Consequently, this invention avoids the problems associated with this wear.

Still another feature of the saw and saw blade assembly of this invention, is that the oscillating portion of the saw, blade 112, is relatively short. Consequently, the mass moment of inertia of the blade, i.e. the inherent ability of the blade to resist changes in rotational speed, is relatively small in comparison to longer conventional blades. Since the mass moment of inertia of the saw blade is relatively small, large amounts of force do not have to be applied to the blade in order to cause it to oscillate in the desired back-and-forth pattern. Given that only small amounts of force are applied to the blade, the resultant vibrations induced by the oscillatory movement of the blade are likewise reduced in comparison to those produced when a conventional saw blade is oscillated.

Since the only portion of the saw blade assembly 22 that moves is the saw blade 112, the mass moment of inertia of the saw blade assembly 22 of this invention is independent of the length of the guide bar assembly 110. This means a saw blade assembly 22 that includes a guide bar assembly 110 with a length of about six inches or more would have associated with it the same mass moment of inertia that is present with a saw blade assembly that has a guide bar assembly of shorter length. (This assumes both saw blade assemblies 22 are provided with the same size saw blade 112.) Thus, using saw 20 with a relatively long saw blade assembly 22 does not result in the saw vibrating appreciably more than one when a shorter blade assembly is used. These long length saw blade assemblies are well suited to make cuts in bone exposed using a minimally invasive surgical technique, and are otherwise difficult to access. Thus, the saw of this invention can be used to perform minimally invasive surgery with a relatively long blade assembly without vibrating significantly more than when the saw is used to perform a procedure with a short-length blade assembly.

Still another benefit of the saw and saw blade assembly of this invention is that since the saw blade 112, and not the guide bar assembly 110, is the oscillating component, the guide bar assembly 110 can be made relatively thick without increasing the mass moment of inertia of the saw blade assembly 22, while still maintaining a thickness which is small enough to be inserted into the kerf made in the bone by the blade head 166. It may be useful in some embodiments to construct the guide bar assembly 110 so that it is relatively thick, i.e. having a depth greater than the dimensions stated above, when providing a relatively long length guide bar assembly. The increased thickness of the guide bar assembly reduces the flexibility of the assembly. This is desirable when providing a long length saw blade assembly 22 designed to perform a minimally invasive surgical procedure.

The fact that the guide bar assembly 110 stays static further makes it possible to use the saw 20 of this invention with the complementary cutting guide 180. Cutting guide 180, unlike a conventional cutting guide, does not require a top wall to define a guide slot or side members to support a top wall-defining upper member. Thus, cutting guide 180, since it does not have the structural members of conventional slot-defining cutting guides, is smaller in size than conventional cutting guides, and thus provides greater visibility to the surgeon. Further, since there is no contact between the oscillating saw blade 112 and the guide surface 194, galling of the guide surface 194 is prevented.

Collectively, it should be further understood that the saw blade assembly of this invention is designed so that when the saw is actuated, the saw blade moves in an arc of at least about 8° and more preferably approximately 10°, (5° on both sides of the longitudinal centerline of the guide bar assembly). Constructing the saw and saw blade assembly of this invention so that the saw blade moves to this extent results in the blade moving over the same arcuate distance as a conventional sagittal saw blade, i.e. where a blade is pivotally attached to the head. Thus, since the sweep of the blade of this invention is the same as the blade sweep of a conventional blade assembly, a surgeon will not have to modify his/her practices significantly to adjust for the use of this invention. It is anticipated that when the saw is actuated, blade 112 will engage in between about 8,000 and about 16,000 complete back-and-forth oscillations per minute.

Figure 11B:
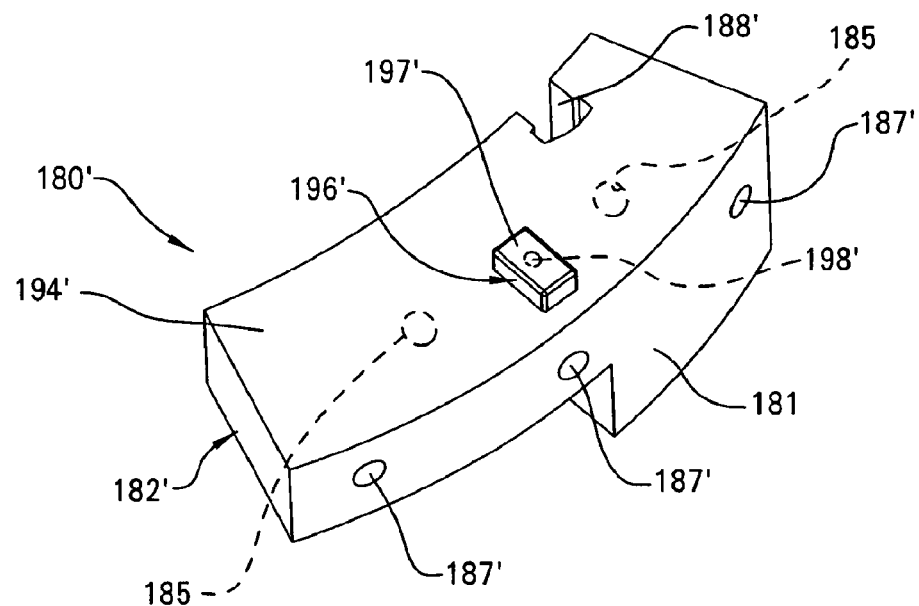
FIG. 11B is a top perspective view of an alternative cutting guide.
Figure 11C:
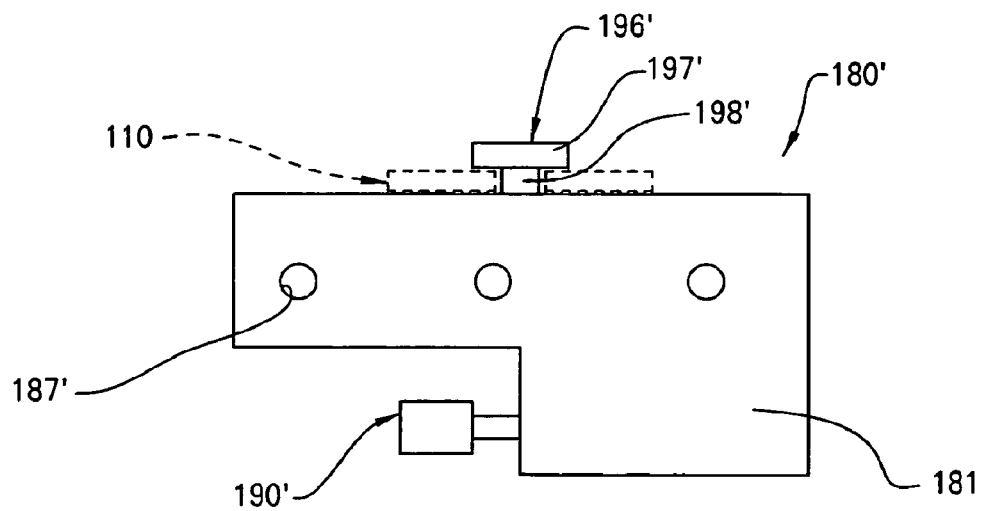
FIG. 11C is a side view of the cutting guide of FIG. 11B.

FIGS. 11B and 11C illustrate an alternative cutting guide 180'. Cutting guide 180' is similar to cutting guide 180, and therefore the same reference numbers are utilized for similar components, plus a "prime".

Cutting guide 180' is defined by a generally L-shaped body or block 182'. Block 182' is secured to a bone with pins (not shown) which extend through bores 187' defined in block 182'. Groove 188' is defined in block 182' for receiving an alignment rod. A thumb screw 190' in this embodiment is mounted to the short downwardly projecting portion 181 of the block 182' which extends below the long upper section thereof, which thumb screw 190' projects into the groove 188' to temporarily secure guide 180' to the alignment rod.

In this embodiment, a capture pin or capture element 196' is mounted to block 182' and projects upwardly from guide surface 194'. Capture pin 196' includes an upper part or head 197' spaced upwardly from guide surface 194' by a stem 198' which extends between surface 194' and the underside of head 197'. Stem 198' has a cross-section which is less than that of head 197', and is sized to allow same to travel within guide slot 132 of guide bar assembly 110. Head 197' is sized to allow same to pass through wide diameter opening 133 of the guide bar assembly 110. The cutting guide 180' is used in a similar manner as guide 180, and maintains guide bar assembly 110 between head 197' and surface 194' during the cutting procedure.

Figure 18:
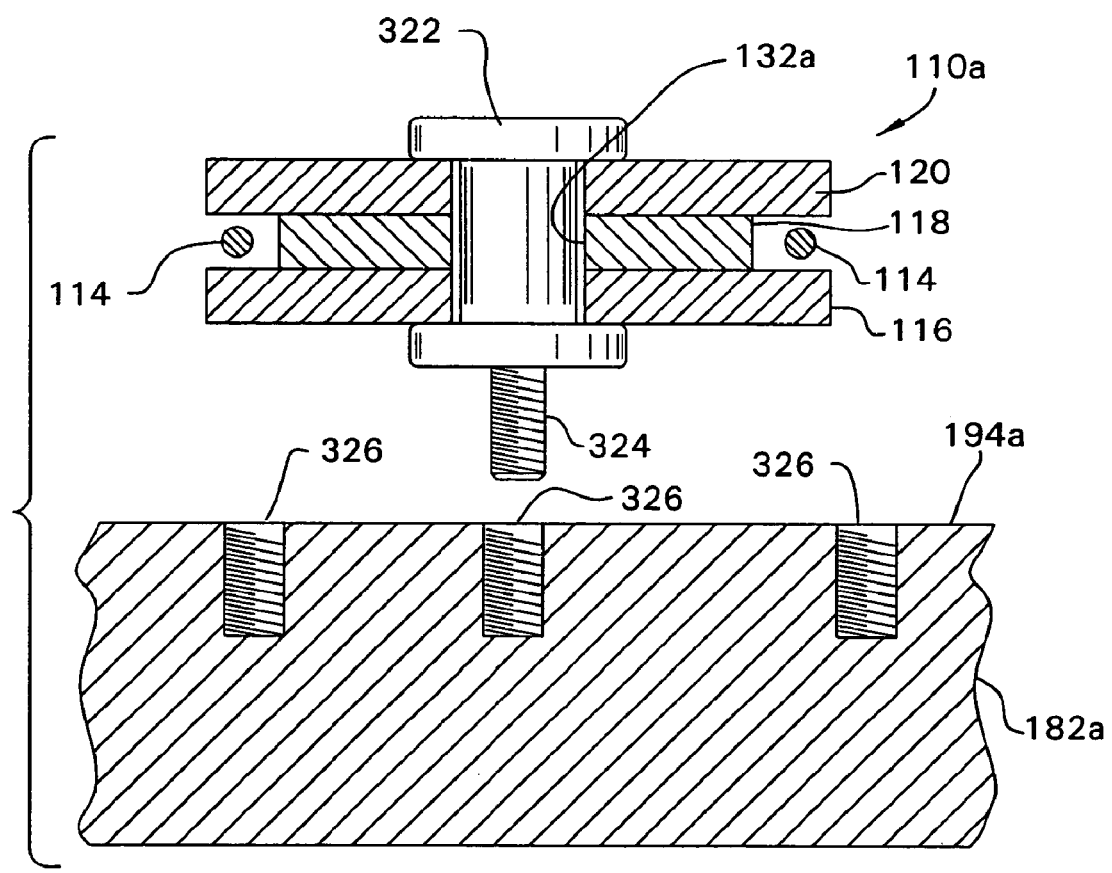
FIG. 18 is a side and cross-sectional view of an alternative means of attaching the saw blade to the cutting guide of this invention.

As shown in dotted lines in FIG. 11B, the capture pin 196' can be removably mounted to block 182', and block 182' can be provided with multiple mounting locations 185 (shown in dotted lines) to allow selective positioning of capture pin 196' along guide surface 194'. An example of a threaded-type of removable mounting is illustrated in FIG. 18 as discussed below.

It will be appreciated that cutting guides 180 and 180' are only examples of cutting guides which may be used according to the invention, and that other cutting guides may be utilized for securing to other locations along the tibia or for attachment to other bones. Further, while cutting guides 180 and 180' are described herein with reference to guide surfaces 194 and 194', respectively, it will be understood that such guides may be provided with multiple guide surfaces, if desirable or necessary. In this regard, block 182 can be provided with additional tracks similar to track 195 which open through the respective guide surfaces. Likewise, block 182' can be provided with additional mounting locations 185 on the respective guide surfaces.

Figure 12:
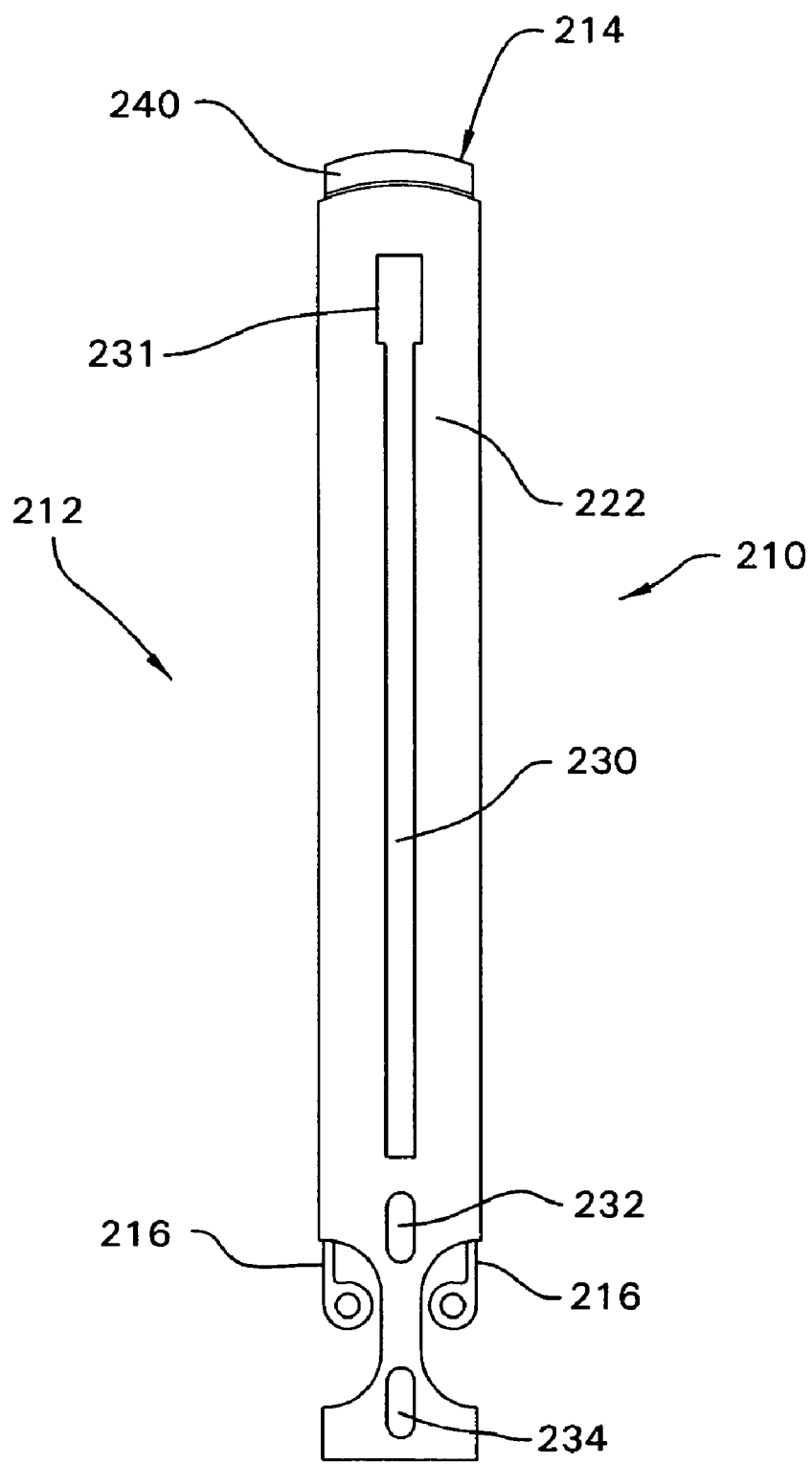
FIG. 12 is a plan view of an alternative saw blade assembly of this invention.
Figure 13:
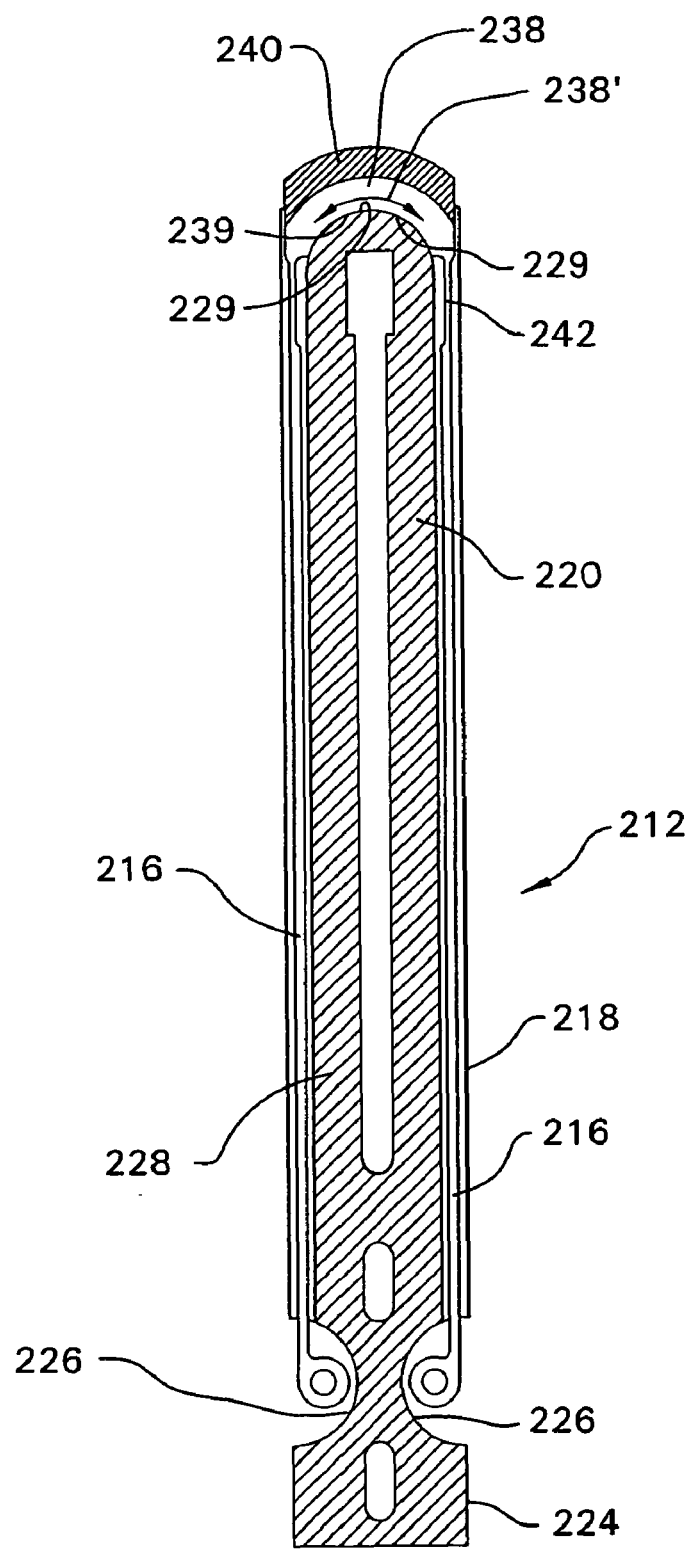
FIG. 13 is a partially disassembled plan view of the saw blade assembly of FIG. 12, with the outer bar removed.
Figure 14:
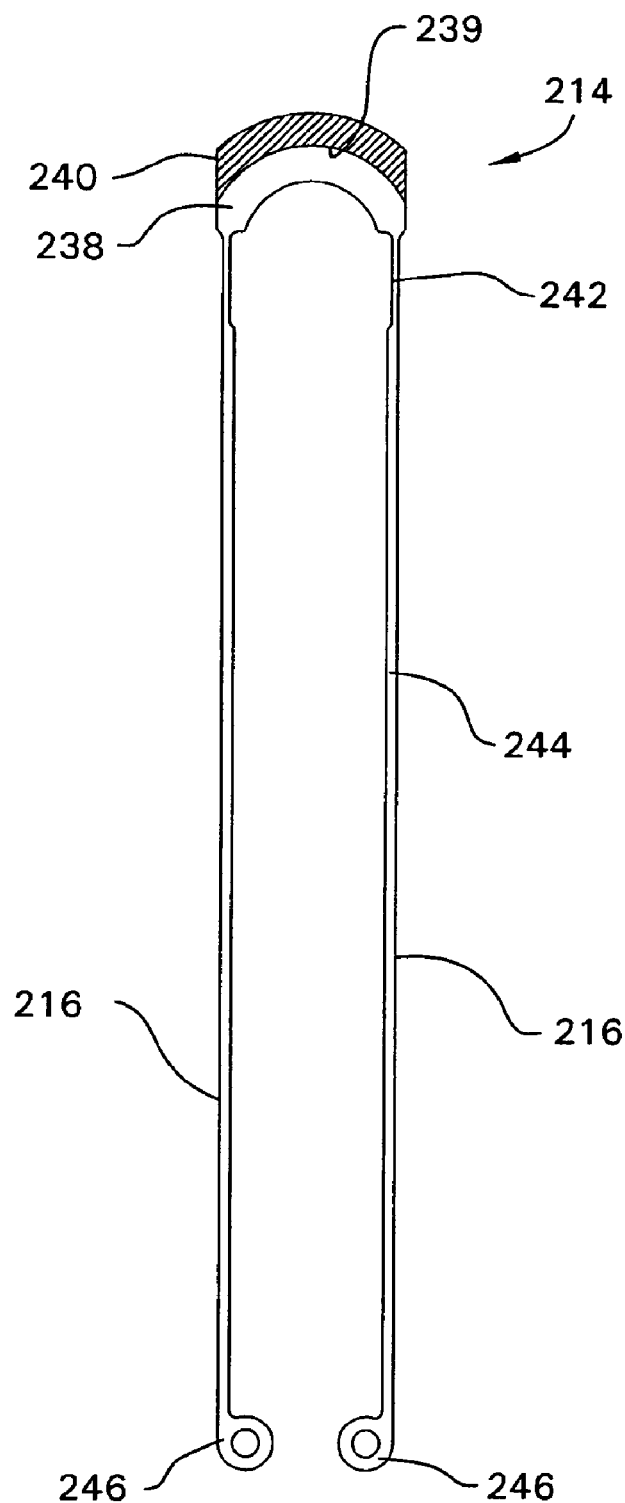
FIG. 14 is a plan view of the saw blade of FIG. 13.

FIGS. 12-14 illustrate an alternative saw blade assembly 210 of this invention. Saw blade assembly 210 includes a guide bar assembly 212. A saw blade 214 is pivotally mounted to the guide bar assembly 212 to extend out of the distal end of the guide bar assembly. Two drive rods 216 are integrally formed with the saw blade 214 and extend proximally rearward from the opposed sides of the saw blade. Each drive rod 216 is connected to a one of the oscillating bar pins 85.

Guide bar assembly 212 includes a bottom bar 218, an inner bar 220 and an outer bar 222. Bottom bar 218 and outer bar 222 are identically shaped and have the general shape of the previously described bottom and outer bars 116 and 120, respectively, of guide bar assembly 110.

Inner bar 220 has a proximal end 224 identical in shape to that of the proximal ends of the surrounding bottom and outer bars 218 and 222, respectively. Forward of the proximal end 224, inner bar 220 is formed to have two symmetric inwardly directed cutouts 226 that define a surface area identical to those defined by the cutouts integral with the bottom and outer bars 218 and 222, respectively. Forward of the cutouts 226, inner bar 220 has a main section 228 that extends distally forward. The inner bar 220 is shaped so that main section 228 has a width that is narrower than the width of the surrounding sections of the bottom and outer bars 218 and 222, respectively. The inner bar 220 is further shaped so that the main section 228 gives the inner bar an overall length that is slightly less than the overall length of the bottom and upper bars 218 and 222, respectively. The main section 228 is shaped to have a distal end front face 229 that has a curved profile.

Guide bar assembly 212 is assembled by stacking the bottom, inner and outer bars 218, 220, and 222, respectively, together. A common slot 230, oval openings 232 and 234, and opening 231 are formed in the bars 218-222 in a single operation. Slot 230 extends close to the distal end of the guide bar assembly 212 in which the distal end of the inner bar 220 that defines front face 229 is located, and terminates in the rectangular opening 231 which is contiguous with slot 230. The abutting edge surfaces of the bars 218-222 that define slot 230 and openings 232 and 234 are welded together to secure the bars together.

Saw blade 214 and drive rods 216, now described by reference to FIG. 14, are formed from a single piece of metal such as 420 stainless steel. Saw blade 214 includes an arcuately shaped base 238. Extending forward from base 238, saw blade 214 in the illustrated embodiment has an arcuately shaped head 240. It will be appreciated, however, that the head 240 may have other configurations. Head 240 is the portion of the saw blade 214 that extends forward from the guide bar assembly 212 and is the portion of the saw blade on which the teeth are formed. Head 240, like previously described saw blade head 166, is larger in thickness than the proximal located base 238 to which the head is attached. Saw blade head 240 is of a relatively large thickness for the same reason saw blade head 166 is similarly shaped.

Drive rods 216 extend proximally rearward from the opposed side edges of the blade base 238. The portion of each drive rod 216 that is actually attached to the blade base 238 is a narrow width finger 242. Extending proximally from the finger 242, each drive rod 216 has a main section 244 which has a slightly greater width than finger 242. More particularly, it will be observed that the fingers 242 are located so that their outer surfaces are in line with the outer surfaces of the rod main sections 244. A ring 246 similar in shape and identical in function to drive rod ring 170 is integrally attached to the proximal end of each drive rod main section 244.

Saw blade 214 will have the same general side-to-side width and thickness as blade 112. The length of the blade, along a radial line from a proximal end edge of the base 238 to the distal point of a tooth will usually be less than about 1.0 inches and, more particularly, less than about 0.5 inches.

The saw blade assembly 210 of this embodiment of the invention is assembled together by inserting the saw blade 214 between the bottom and outer bars 218 and 222, respectively, of the guide bar assembly 212. The saw blade 214 is positioned so that the proximally facing curved end 239 of the blade base 238 abuts the similarly curved distal facing face 229 of the inner bar 220. Drive rods 216 extend in the space between the bottom and outer bars 218 and 222, respectively, adjacent the opposed sides of the inner bar 220. The proximal ends of the drive rods 216 and the associated rings 246 extend into the open space of the guide bar assembly proximal end cutouts as shown in FIG. 12.

The saw blade assembly 210 of this version of the invention is fitted to saw 20 and used in the same general manner as saw blade assembly 22. The proximal end of the guide bar assembly 212 is seated in groove 46 within saw head 38. The fasteners used to hold cover 91 to the saw head 38 extend through openings 232 and 234 to hold the guide bar assembly 212 to the head 38. Drive rod rings 246 are fitted over pins 85 to connect the saw blade to the oscillating bar 86.

A saw 20 with blade assembly 210 of this invention is used in the same general manner as a saw 20 with blade assembly 22. In this embodiment, the fingers 242 are flexible, such that when drive rods 216 reciprocate in opposite directions, the curved end 239 of blade base 238 moves in a reciprocating manner over the distal facing face 229 of the inner bar 220, as indicated by arrow 238' in FIG. 13, which in turn causes side-to-side pivoting movement of the blade head 240 across the distal end of the guide bar assembly 110. Thus, flexible fingers 242 allow the base 238 and head 240 to pivot relative to the distal end of the guide bar assembly 212.

It will be noted that the slot 230 of guide bar assembly 212 extends further distally along the assembly than slot 132 of guide bar assembly 110. This may make it possible to place a capture pin of the cutting guide designed to be used with guide blade assembly 212 closer to the bone to be cut than is possible with a cutting guide 180 designed to be used with guide bar assembly 110.

Figure 15:
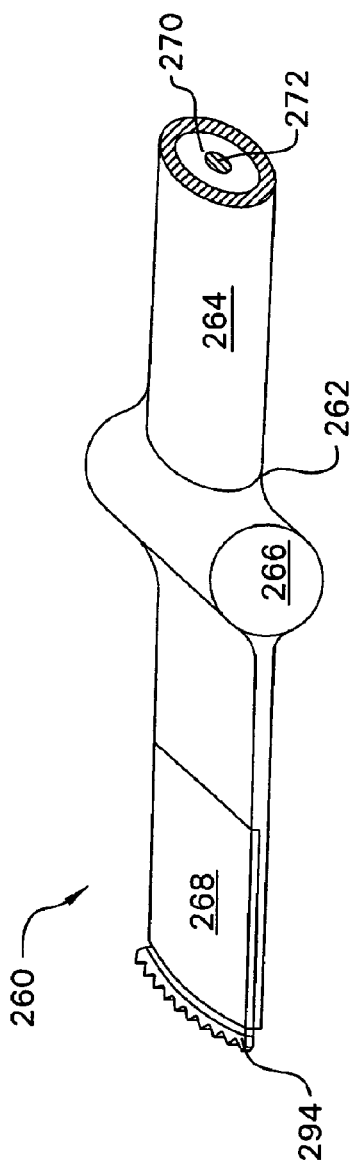
FIG. 15 is a perspective view of the distal end of an alternative saw assembly of this invention.
Figure 16:
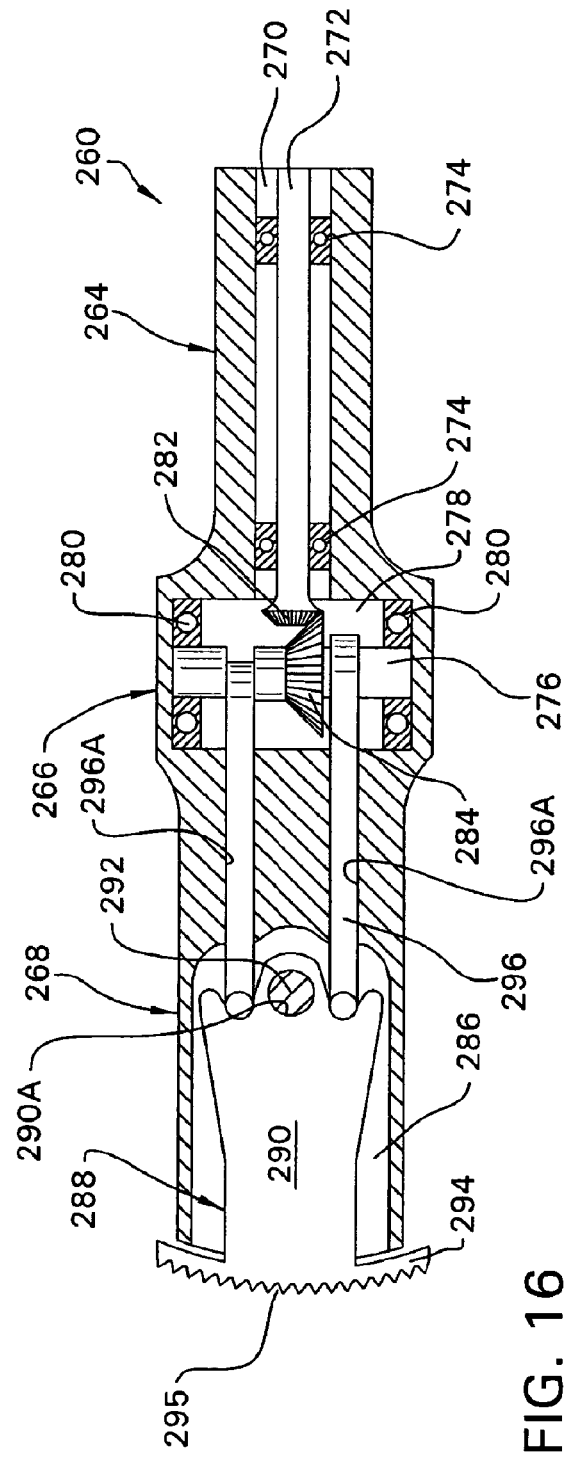
FIG. 16 is a plan view of a partially disassembled saw blade of FIG. 15.

FIGS. 15 and 16 illustrate the distal end of an alternative saw blade assembly 260 of this invention. Assembly 260 includes a housing 262 that extends forward from the distal end of the handpiece. Housing 262 has a proximal section 264 that is generally cylindrical and that extends forward from the handpiece. Forward of proximal section 264, housing 262 has a middle section 266 that is cylindrical and arranged so as to have a longitudinal axis that is perpendicular to the longitudinal axis of the proximal section 264. Forward of middle section 266, housing 262 has a forward extending planar distal section 268. Distal section 268, it will be understood, is longitudinally axially aligned with proximal section 264. Owing to its planar shape, distal section 268 is understood to be the guide bar of saw blade assembly 260.

Housing proximal section 264 is formed with a longitudinally extending through bore 270 in which a drive shaft 272 is disposed. Also seen in the drawings are bearing assemblies 274 that rotatably support the drive shaft 272 in bore 270. The drive shaft 272 is connected to a crank 276 that is rotatably mounted in a cylindrical space 278 within housing middle section 266. Bearing assemblies 280 rotatably hold crank 276 in the housing middle section 266.

Drive shaft 272 is formed with a head 282 that is in the form of a bevel gear. The shaft head 282 engages a complementary bevel gear 284 formed integrally with the crank 276 so that rotation of the drive shaft 272 results in like movement of the crank 276.

Housing distal section 268 is shaped to define a planar blade space 286 that extends proximally rearward from the open front end of the housing 262. A saw blade 288 is pivotally mounted in blade space 286. The saw blade 288 consists of a planar, bar-like base 290. A pivot pin 292 integral with the housing distal section extends through an opening 290A in the proximal end of the blade base 290 to pivotally hold the blade 288 to the housing 262. In the illustrated embodiment, saw blade 288 is further formed to have an arcuately shaped head 294 with teeth 295, which head 294 is attached to the distal end of the blade base 288. Head 294 is the only portion of the blade 288 that is located outside of housing 262 and is located adjacent the distal front end of the housing.

A pair of push rods 296 connect the saw blade 288 to the crank 276. The push rods 296 are located in parallel spaced apart slots 296A formed in the housing distal section 268. The distal ends of the push rods 296 are connected to the proximal end of the saw blade base 290 on opposed sides of the pivot pin 292. The distal end of each push rod 296 is pivotally attached to the adjacent proximal end of the adjacent blade base 290. The proximal end of each push rod is connected to the crank 276. The proximal end of each push rod 296 is connected to a pin integral with the crank 276 that is axially offset from the center axis of the crank. Collectively, the pins to which the push rods 296 are connected are diametrically opposed to each other relative to the center axis of the crank 276.

While not illustrated, it should be understood that the housing distal section 268 of this embodiment of the invention may be provided with a longitudinally extending guide slot to facilitate the insertion of the cutting guide capture pin.

Saw and blade assembly 260 of this version of the invention is used by actuating the saw motor so as to cause drive shaft 272 to rotate. The rotation of the drive shaft results in the like rotation of crank 276. The rotation of the crank causes push rods 296 to reciprocate back-and-forth. More particularly, owing to how the push rods are connected to the crank 276, as one push rod is urged forward, towards the distal end of the housing, the other push rod is pulled in the opposite direction. The reciprocating movement of the push rods 296 causes a like side-to-side reciprocating or oscillating movement of the saw blade 288.

It should be understood that the foregoing is directed to specific versions of this invention and that other versions of this invention may vary from what has been described.

For example, in the above description, in order to remove saw blade 112 from the guide bar assembly 110, it is necessary to remove the cover 91 from the saw head 38 and wholly remove the saw blade assembly 22 from the saw head. Alternatively, it may be possible to simply loosen the fasteners 93 that hold saw cover 91 to the head 38. Since the guide bar assembly openings 134 and 136 through which the fasteners 93 extend are oval in shape, once the screws are so loosened, one could then push the guide bar assembly 110 rearwardly. The rearward movement of the guide bar assembly 110 exposes the proximal end of the saw blade 112 so the blade can be removed and new blade connected to the drive rods 114.

In still another alternative version of the invention, the guide bar assembly 110 is moveably attached to the saw head 38 such that the guide bar assembly is able to slide towards or away from the saw handpiece 24. A thumb screw or clamp is set to normally hold the guide bar assembly 110 in the most forward distal position. When it is desirable to remove and replace the saw blade 112, the thumb screw/clamp is set to release the clamping force against the guide bar assembly. Manual force is used to push the guide bar assembly 110 towards the handpiece 24. This displacement of the guide bar assembly 110 exposes the proximal base 148 of the saw and the distal end heads 172 of the drive rods 114. The exposure of these components makes it possible to remove the attached saw blade 112 from the drive rods 114 and attach a replacement blade. The thumb screw/clamp is then reset to the position in which it locks the guide bar assembly 110.

In these versions of the invention, a spring may be seated in the head to bear against the guide bar assembly 110. The spring would urge the guide bar assembly to the most distal position. However the thumb screw/clamp is also provided since when the saw is pressed against the bone, unless there is a locking mechanism, the whole of the saw blade assembly 22 would be forced rearwardly. Alternatively, a single camming mechanism may be provided to both normally hold the guide bar assembly in the most forward position and retract the assembly when it is necessary to change saw blades 112.

Also, it should likewise be understood that the disclosed type of motive power used to actuate the saw blade of this invention is understood to be illustrative, and not limiting. There is no requirement that all versions of this invention include handpieces that are battery powered. The invention can be, if appropriate, constructed using versions of this invention wherein the electric power to supply the motor comes from a power supply over a corded link. Also, similarly, the invention is not limited to handpieces that include electric powered motors. In some versions of the invention, it may be desirable to provide the handpiece with a pneumatically driven motor. In these versions of the invention, the compressed air used to actuate the motor is supplied to the handpiece from a hose connected to an air supply.

Moreover, there is no requirement that a power-producing motor be provided in each handpiece of the saw of this invention. It may be desirable to provide a version of the saw of this invention wherein the motive unit that generates power is a unit that is separate from and located proximal to the handpiece. In these versions of the invention, a flexible drive shaft or a drive cable that extends between the unit with the motor and the distal located handpiece from which the guide bar and saw blade extend may be utilized.

Likewise, it should be recognized that the handpiece shape is understood to be merely exemplary. In an alternative version of the invention, the handpiece may have an elongated cylindrical shape. This would allow the surgeon to hold the handpiece much as he/she would hold a large marker.

Alternative means to oscillate the saw blade may be employed. For example, there is no requirement that in all versions of the invention two drive rods/push rods be employed. A version of this invention in which a single drive rod/push rod that reciprocates back-and-forth oscillates the saw blade may also be possible. The invention could even be provided with three or more drive rods that actuate the saw blade.

Figure 17:
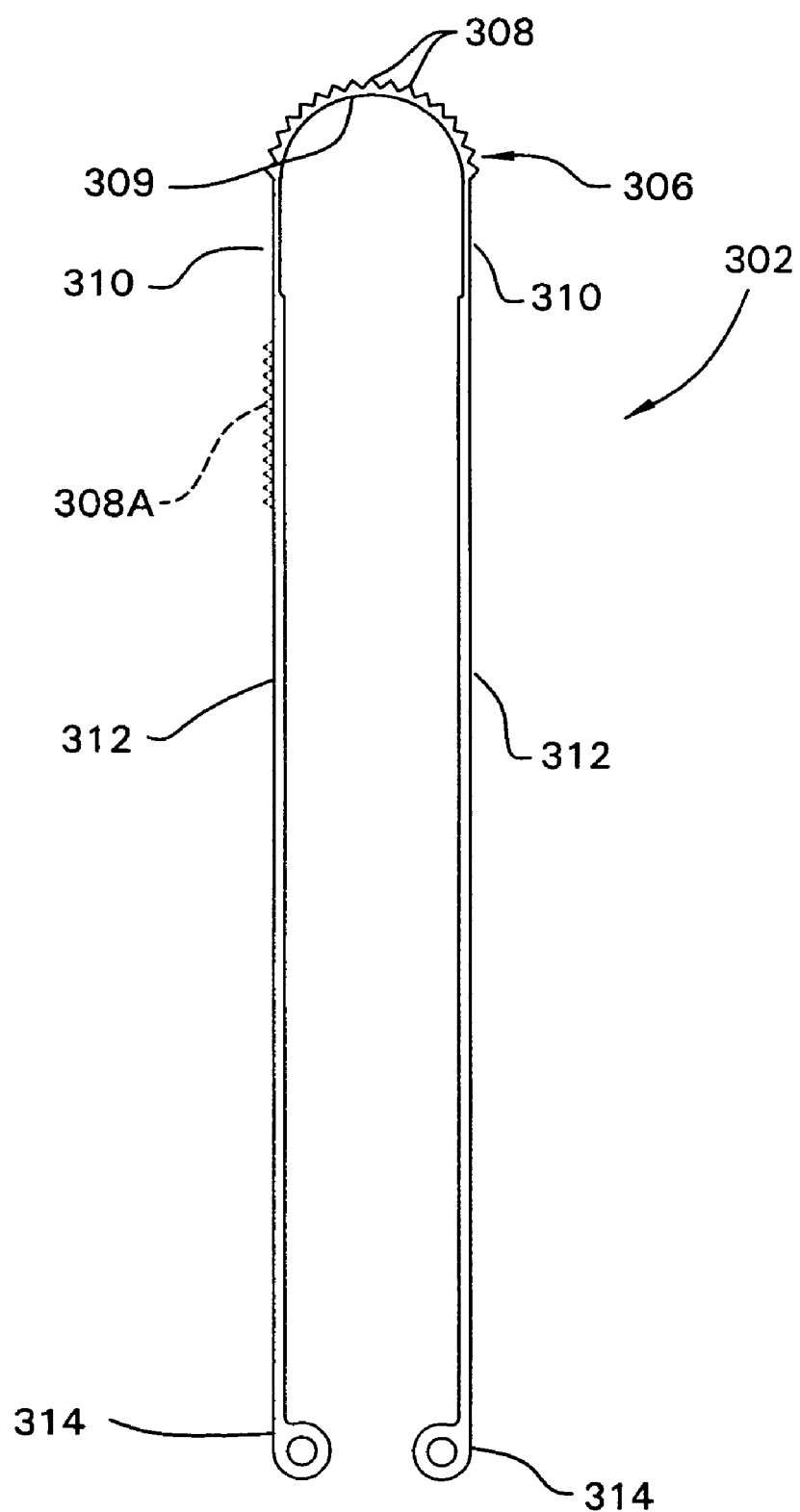
FIG. 17 is a plan view of an alternative saw blade of this invention.

Similarly, there is no requirement that in all versions of the invention, the blade consist of a rigid member from which teeth extend distally outward. In some versions of the invention, the saw blade may actually be a section of a flexible band of metal. As seen in FIG. 17, in these versions of the invention, a band 302 is formed with a distal end section 306 from which teeth 308 extend outwardly. This distal end section 306, it is observed, includes both an arcuate center portion 309 and two opposed side portions 310. Extending proximally from the opposed side portions 310, band 302 has proximal sections 312. Rings 314 are attached to the proximal ends of the proximal sections 312. In the depicted version of the invention, the cross-sectional width of the proximal sections 312 is greater than that of the distal end section 306 though that may not always be the case.

In this embodiment, the distal end section 306 of the band 302 forms the actual saw blade. This band is wrapped around the guide bar assembly. More particularly, the front end of the guide bar assembly may be formed with a forward-facing groove in which the center section of the band is seated. The more proximal portions of the guide bar assembly are formed with channels for accommodating the side sections of the band. Rings 314 at the proximally located ends of the band 302 connect the band to oscillating bar 86.

In this version of the invention it will be noted that teeth 308 not only project outwardly from the front center section 309 of the saw blade, they also project out from the side portions 310. Thus, this version of the invention is useful if one wants to cut from the side edge of the guide bar assembly. As shown in dotted lines in FIG. 17, teeth 308A may also be provided on one or both proximal sections 312 of band 302 which would project sidewardly through a corresponding opening in the guide bar assembly.

Moreover, it should be appreciated that, in versions of the invention with rigid saw blades, there is no requirement that the complementary connecting members that extend to the reciprocating drive assembly in the handpiece be rigid drive rods. In some versions of the invention, flexible drive cables may be employed as the connecting members.

Also, there is no requirement that, in all versions of the invention, the connecting members that extend from the drive assembly extend internally through the guide bar to the extent the described and illustrated connecting members extend through the guide bar. In some versions of the invention, the connecting members may be seated in grooves formed in an outer side or edge surface of the guide bar. The connecting members may also, along a substantial length of the guide bar, simply lie adjacent the guide bar.

It should similarly be recognized that alternative mechanisms other than the described ring-over-pin may be used to connect the saw drive rods to the oscillating assembly. In some versions of the invention, the oscillating bar may be formed with slots. The proximal ends of the drive rods are dimensioned to tightly fit in the slots. Stops are integrally attached to the drive rods so as to be located on opposed sides of the section of the rod seated in the oscillating bar slots. Thus, the presence of the stops ensures that the oscillations of drive rods will cause reciprocal motion of the drive bar. Further, oscillating bar 86 which is pivoted or oscillated about the axis defined by head drive shaft 50 may be replaced with a pair of pins or pegs which move linearly and reciprocate in opposite directions.

It should likewise be understood that there may be variations in how the saw of this invention is used with the cutting guide. For example, there is no requirement that in all versions of this invention the cutting guide be used with a saw blade that oscillates. In some versions of this invention, it may be desirable to provide a saw with a blade that is in the form of an endless band. In these versions of the invention, the band may be driven in a single direction or, alternatively, oscillate. In either version, the band will be mounted to a planar guide bar assembly similar to one of the above illustrated and described assemblies. In these versions of the invention, the guide bar assembly will have the guide slot previously described to facilitate the seating of the cutting guide capture pin 196.

As discussed above with respect to cutting guide 180' of FIGS. 11B and 11C, the capture pin may be removably attached to the cutting guide and the cutting guide provided with a number of different means for holding the capture pin at different points along the guide surface of the cutting guide. An advantage of this arrangement allows the point on the guide surface of the cutting guide at which the guide bar is held to be selectively set.

For example, as seen by FIG. 18, an alternative capture pin 322 may have a generally spool-like shape. The capture pin 322 is assembled so that the narrow diameter center section of the pin slidably fits in the longitudinally extending slot 132a of a guide bar assembly 110a. Given the permanent or semi-permanent mounting of the capture pin 322 to the guide bar assembly 110a, there may not be a need to form the guide bar assembly with an opening integral with the slot 132a to facilitate the seating and removal of the guide pin. Here, the guide pin 322 has a downwardly directed threaded stem 324. In these versions of the invention, the cutting guide block 182a is formed with a number of spaced apart threaded bores 326 that extend inwardly from the guide surface 194a. The bores 326 are each shaped to releasably hold the capture pin stem 324.

Alternatively, in these versions of the invention, a spring-biased ball mounted to either the capture pin or the cutting guide may be used to releasably hold the pin to the cutting guide. A toggle clamp mechanism may also be employed to hold the capture pin to the cutting guide.

An advantage of the above-described versions of the invention is that it would allow the surgeon in a single operation to attach both the capture pin 322 and the saw to the cutting guide at the appropriate surface point along the cutting guide.

Likewise, the cutting guide may have alternative constructions from what has been described and illustrated. At the simplest, a cutting guide may be formed to have plural guide surfaces each provided with a capture pin for restraining and guiding the guide bar during the cutting process. Also, it should be recognized that the illustrated version of the invention, wherein the cutting guide guide surface essentially abuts the bone, is exemplary, and not limiting. In some versions of the invention, the cutting guide may be shaped so as to have a guide surface that is spaced from the tissue or bone in which the cut line defined by the guide surface is to be formed. This version of the invention may be especially useful in minimally invasive surgical procedures since it would minimize the amount of hardware it would necessitate placing in close physical proximity to the bone on which the surgical procedure is to be performed.

Moreover, while not illustrated, it should be recognized that it may be desirable to provide the portion of the cutting guide block that defines the proximal facing edges of the guide surface with posts. These posts would be offset from the capture pin. The posts would be provided if it is desirable to limit the extent to which the guide bar is able to pivot around the capture pin.

Some versions of the invention provided with the posts may be constructed so that the posts are spaced essentially the width of the guide bar assembly. The posts would thus essentially stop pivoting of the guide bar assembly 110 and the saw 112. In these versions of the invention, the guide bar assembly may be provided with a small arcuate slot that extends inwardly from the side. A precise arcuate cut is made by pushing the saw blade assembly forward until the slot goes into registration with the post. The guide bar assembly is then pivoted to the extent the cutting guide post seats in the guide bar side slot.

It should likewise be recognized that alternative means may be provided to hold the cutting guide in a fixed position relative to the bone to be cut. For example, a brace assembly may be used to both hold the bone steady and hold the cutting guide in a fixed position relative to the bone and also in a position that is away from the bone. Thus, in this particular version of the invention, since the cutting guide is spaced away from the bone, it would reduce the need to make incisions around the bone to facilitate cutting guide placement. Thus, this particular version of the invention would further facilitate cutting the bone using a minimally invasive surgical procedure.

Figure 19:
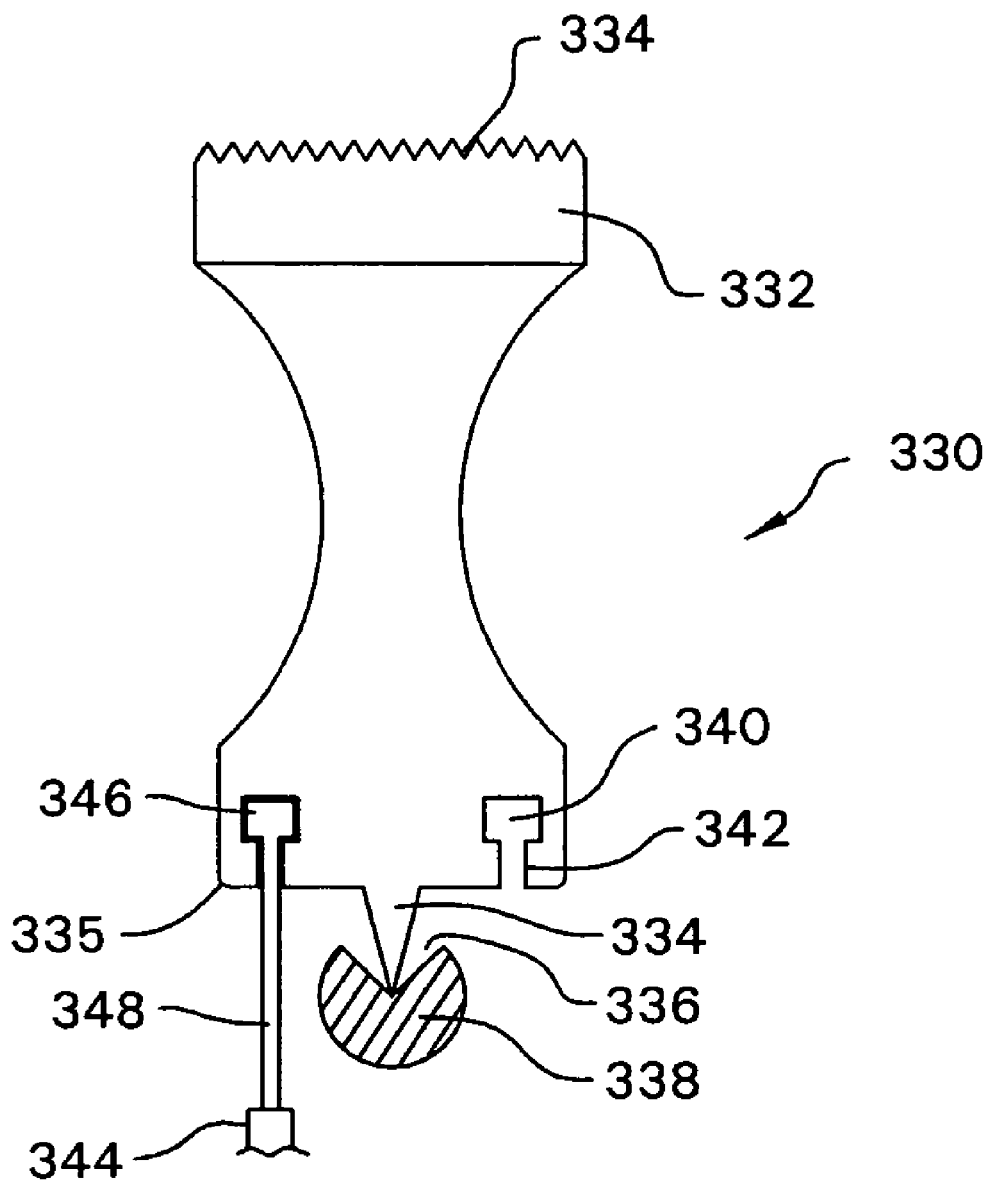
FIG. 19 depicts the features of an alternative saw blade of this invention and how the saw blade is pivotally mounted to the complementary guide bar assembly.

Moreover, the saw blades may have shapes and features different from what has been shown. For example, saw blades 112 and 214 are depicted as having heads with arcuately shaped distally directed faces. This is exemplary and not limiting. As depicted in FIG. 19, it may be desirable to provide a saw blade 330 with a head 332 that has a distal facing face 334 that is planar in shape or straight-edged. This version of the saw blade may be provided when it is desirable to provide a saw blade that cuts more aggressively than an arcuate blade.

Saw blade 330 also has a geometric feature to facilitate the pivoting of the blade that is different from that previously described. Specifically, saw blade 330 has a V-shaped pointed tab 334 that extends from the proximally directed end 335 of the blade. Tab 334 seats in a forward opening notch 336 formed in a static component 338 integral with the guide bar assembly to which the saw blade is mounted. In FIG. 19, the static component 338 represents a pivot pin of the guide bar assembly.

Also, there is no requirement that the geometric features that a saw blade is provided with be designed to allow the blade to pivot relative to the associated drive rods. The proximal end of saw blade 330 is provided with square shaped openings 340 that are spaced inwardly from the blade proximal end 335. A small slot 342 extends from each opening 340 to the adjacent proximal end 340.

Saw blade 330 is actuated by drive rods 344. (The distal end of one drive rod shown.) Each drive rod 344 is provided with a square shaped head 346. Thus, the rod heads 346 are dimensioned to fit closely within the complementary saw blade openings 340. Extending proximally from the head 346, each drive rod 340 has a flexible elongated neck 348. The drive rod necks 348 are the portions of the drive rods that extend through and proximally beyond saw blade slots 342. Thus, in versions of the invention in which drive rods 344 are employed, the drive rod heads 346 do not move relative to the saw blade. Instead, the flexibility of the drive rod necks 348 is what allows the pivoting movement of the saw blade relative to the proximal portions of the drive rods 344.

Figure 20:
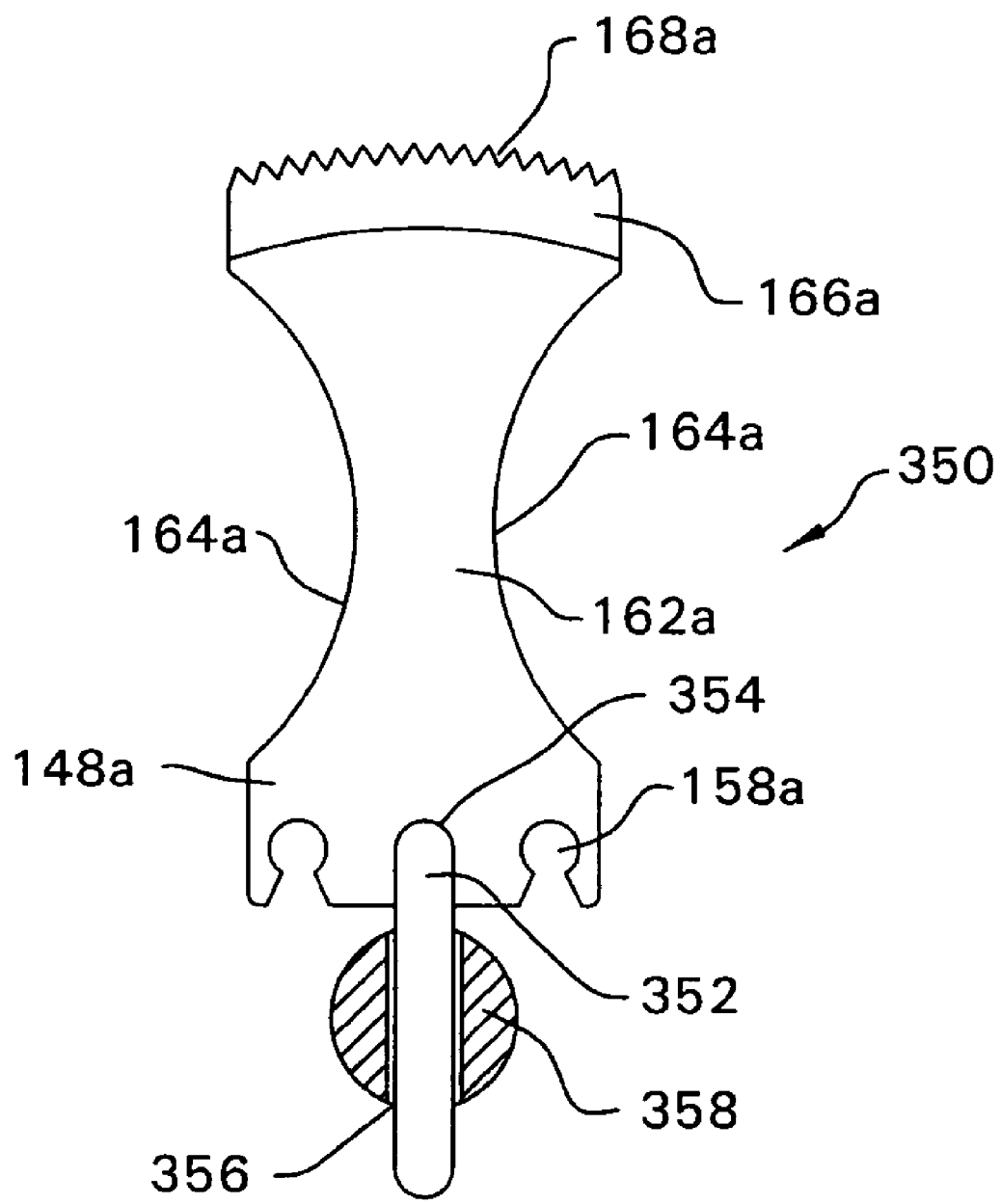
FIG. 20 depicts the features of an alternative saw blade of this invention and how the saw blade is pivotally mounted to the complementary guide bar assembly.

FIG. 20 illustrates still another alternative saw blade 350 of this invention. The distal portions of saw blade 350 are similar to those of the first-described saw blade 112. Saw blade 350 is, however, provided with a tail 352 formed of flexible metal. The distal end of tail 352 seats in a U-shaped slot 354 that extends forward from the proximal end of the blade 350. The portions of the tail proximal to the saw blade 350 seat in a slot 356 formed in a static portion of the guide bar assembly. In FIG. 20, slot 356 is formed in a static pivot pin 358 of the guide bar assesmbly. Tail 352 is thus the component of the saw blade 350 that connects the blade to the complementary guide bar assembly.

It should be clear that the features of saw blades 330 and 350 may be individually incorporated into the other described saw blades of this invention.

Also, the described and illustrated versions of the guide bar assembly are of uniform thickness along their lengths. This should not be understood to be limiting. In alternative versions of the invention, the guide bar assembly may have a thickness that varies along the length. For example, it may be desirable to construct the guide bar assembly so the proximal portion has a thickness greater than the distal portion. This construction may be appropriate in order to reduce the flexibility of the guide bar assembly.

Moreover, in the described versions of the invention, the angular positions of the guide bar assemblies relative to the handpieces from which the assemblies extend are fixed. This need not always be the case. In some versions of the invention, it may be possible to construct the invention so the angular position of the guide bar assembly, and therefore of the attached saw blade, relative to the handpiece is selectively set. This may be accomplished by providing a version of the invention in which the handpiece head and the drive assembly components internal to the head are able to rotate around the axis of the handpiece drive shaft that actuates the drive assembly. This would make it possible to set the angular orientation relative to the longitudinal axis of the handpiece of the plane in which the guide bar is oriented and in which the saw blade oscillates. Thus, one guide bar assembly-and-saw blade orientation would be the illustrated orientation wherein the blade is in a plane located about the drive shaft axis. By resetting the orientation of the head, the saw blade could be placed in a plane that is to the side of the drive shaft axis or even in a plane below the drive shaft axis.

An advantage of these versions of the invention is that it would allow the surgeon to set the position of the saw blade so that it is in an optimal location to facilitate the ergonomic use of the saw of this invention.

Figure 21:
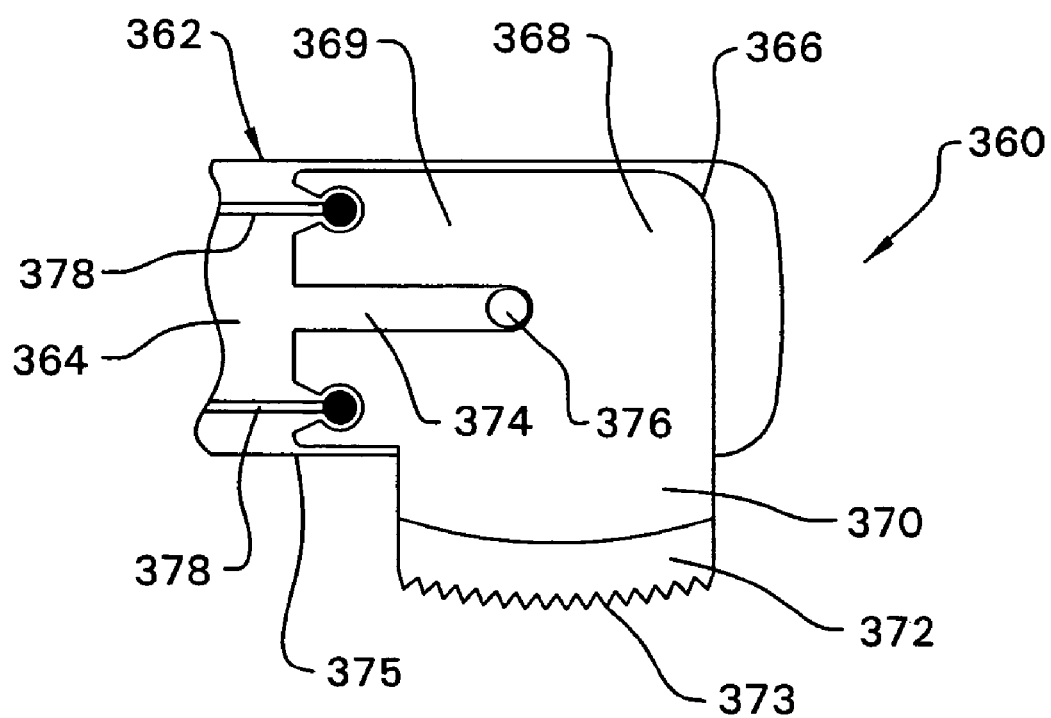
FIG. 21 depicts the features of another alternative saw blade assembly of this invention.

Moreover, while it is anticipated that, in many versions of the invention, the saw blade will project forwardly from the distally directed front face of the guide bar, that may not always be the case. FIG. 21 illustrates an alternative saw blade assembly 360 of this invention. Saw blade assembly 360 includes a guide bar assembly 362 of which only a single outer bar 364 is shown.

A saw blade 366 is disposed inside the distal end of the guide bar assembly 362. Saw blade 366 has an L-shaped base 368 having proximal end 369 with a longitudinal axis that is normally parallel to, if not aligned with, the longitudinal axis of the guide bar assembly 362. Base 368 also includes a front end 370 forward of the proximal end that has a longitudinal axis perpendicular to the longitudinal axis of the guide bar assembly. A saw head 372 with teeth 373 extends forward from the front end 370 of the saw blade base 368.

Collectively, the guide bar assembly 362 and saw blade 366 are dimensioned and arranged relative to each other so that the saw blade head extends out from a side edge 375 of the guide bar assembly immediately proximal to the distally directed front face 372 of the guide bar assembly.

A notch 374 extends forward from the proximal edge of the saw blade base proximal end 369. The saw blade 366 is mounted to the guide bar assembly 362 by positioning the blade so a static pivot pin 376 integral with the guide bar assembly seats in notch 374. Drive rods 378 attached to the saw blade base 368 on opposed sides of the notch 374 connect the saw blade to the drive assembly integral with the saw. Thus, when the saw of this invention is actuated, the drive rods 378 cause the saw blade head to pivot in an arc that is generally parallel to the longitudinal axis of the guide bar assembly.

Saw blade assembly 360 thus provides a version of this invention wherein the blade 366 can be pressed against bone or hard tissue to make a cut that is in a direction perpendicular to the longitudinal axis of the guide bar assembly 362. This may be useful where for surgical reasons it is difficult or undesirable to make a cut through bone or hard tissue from a head-on direction.

In the above described version of the invention, it should be understood that often the pivot pin 376 is positioned on the guide bar assembly 362 so that when the saw blade 366 is fitted over the pin, the curved profile of saw head 372 is generally centered relative to the pin.

It will be appreciated that the means used to transfer the rotary motion of the motor shaft to the drive rods that oscillate the saw blade may be different from what has been described. Thus, the motor output shaft may actuate a crank similar to crank 276. Drive rods similar to drive rods 114 may be attached to the crank. Upon the actuation of the motor, the reciprocal motion of the drive rods would then cause the oscillation of the attached saw blade 112.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A cutting guide and saw blade assembly, said assembly comprising:
    a cutting guide having a body shaped to be positioned against tissue to be cut, said body having: a guide surface that is an exposed surface of said body; and features for receiving fasteners that hold said body to the tissue against which said cutting guide is positioned;
    a saw blade assembly, said saw blade assembly having:
        a bar having opposed proximal and distal ends, the proximal end shaped to be attached to a saw and the distal end having a thickness;
        a blade having a base that is movably mounted in said bar adjacent the bar distal end and a head integral with said base that is located outside of said bar, said head having a thickness at least equal to the thickness of the bar distal end and having teeth; and
        at least one drive rod moveably disposed in said bar, said at least one drive rod having a proximal end shaped to be attached to a driver integral with the saw and a distal end connected to said blade base so that the actuation of said drive rod by the saw driver results in said drive rod oscillating said blade around a pivot point; and
    a coupling assembly having a first feature attached to said cutting guide body and a second feature integral with said saw blade assembly bar, said features configured to moveably hold said saw blade assembly bar to said cutting guide body on the cutting guide guide surface so that, said saw blade assembly bar is able to move over the guide surface and is constrained from movement outside of a plane above the guide surface.

2. The cutting guide and saw blade assembly of claim 1, wherein said coupling assembly is configured to allow said saw blade assembly bar to move, forward, rearward and laterally across the cutting guide guide surface.

3. The cutting guide and saw blade assembly of claim 1, wherein said coupling assembly first feature is mounted to said cutting guide body so as to project above the cutting guide guide surface.

4. The cutting guide and saw blade assembly of claim 1, wherein said coupling assembly first feature is moveably mounted to said cutting guide body so that the movement of said coupling assembly first feature along said cutting guide body results in the movement of said saw blade assembly bar over said cutting guide guide surface.

5. The cutting guide and saw blade assembly of claim 1, wherein:
    said coupling assembly first feature is a pin that is mounted to said cutting guide body that extends above the guide surface; and
    said coupling assembly second feature is an opening formed in said saw blade assembly bar, the opening dimensioned to receive said pin and further dimensioned to allow said bar to both pivot around and engage in back and forth movement relative to said pin.

6. The cutting guide and saw blade assembly of claim 1, wherein:
    said cutting guide body is shaped so that said guide surface is defined by an outer perimeter; and
    said coupling assembly first feature extends upwardly from said cutting guide body so as to extend up from said the guide surface at a location spaced inwardly from the outer perimeter of the guide surface.

7. The cutting guide and saw blade assembly of claim 1, wherein:
    said coupling assembly first feature is provided with a first member for engaging a complementary second member integral with said cutting guide body; and
    said cutting guide body is formed with a plurality of second members so that said coupling assembly first feature can be mounted to said body at a plurality of different locations on said body.

8. The cutting guide and saw blade assembly of claim 1, wherein said saw blade assembly includes two said drive rods that extend from said blade base through said saw blade assembly bar, said drive rods being located on opposed sides of the point around which said blade pivots.

9. The cutting guide and saw blade assembly of claim 1, wherein:
    said cutting guide body is formed to have plural guide surfaces; and
    plural coupling assembly first features are attached to said coupling guide body, said coupling assembly first features being arranged so that said saw blade bar can be moveably held and constrained over at least two of the guide surfaces.

10. A cutting guide and saw blade assembly, said assembly comprising:
- a cutting guide, said cutting guide having:
  - a body shaped to be positioned against tissue to be cut, said body having: a guide surface that is an exposed surface of said body, the guide surface being defined by an outer perimeter; and features for receiving fasteners that hold said body to the tissue against which said cutting guide is positioned; and
  - a coupling component that is mounted to said body and that extends upwardly from said body above the guide surface so as to be located inwardly from the outer perimeter of the guide surface;
- a saw blade assembly, said saw blade assembly having:
  - a bar having opposed proximal and distal ends, the proximal end shaped to be attached to a saw and the distal end having a thickness, said bar further shaped to be releasably attached to said cutting guide coupling component wherein, said cutting guide coupling member and said saw blade assembly bar are collectively configured so that said coupling component holds said saw blade assembly bar against the cutting guide guide surface and said saw blade bar is able to move forward, rearward and across the guide surface and constrains said bar from movement above the guide surface;
  - a blade having a base that is movably mounted in said bar adjacent the bar distal end and a head integral with said base that is located outside of said bar, said head having a thickness at least equal to the thickness of the bar distal end and having teeth; and
  - at least one drive rod moveably disposed in said bar, said at least one drive rod having a proximal end shaped to be attached to a driver integral with the saw and a distal end connected to said blade base so that the actuation of said drive rod by the saw driver results in said drive rod oscillating said blade around a pivot point.

11. The cutting guide and saw blade assembly of claim 10, wherein said coupling component is moveably mounted to said cutting guide body so that said coupling component is able to move above the cutting guide guide surface so that the movement of said coupling component above the guide surface results in the movement of said saw blade assembly bar over the guide surface.

12. The cutting guide and saw blade assembly of claim 10, wherein said coupling component and said saw blade assembly bar are configured so that, when said bar is attached to said coupling component, said bar is able to pivot around an axis that extends longitudinally through said coupling component.

13. The cutting guide and saw blade assembly of claim 10, wherein:
- said coupling component is provided with a first mounting feature for releasably engaging a second mounting feature integral with the cutting guide body; and
- said cutting guide body is shaped to have plural guide surfaces and is further formed to have plural second mounting features, said second mounting features being arranged at different locations on said body so that said coupling component can be mounted to said body to extend above at least two of the guide surfaces.

14. The cutting guide and saw blade assembly of claim 10, wherein said saw blade assembly includes two said drive rods that extend from said blade base through said bar, said drive rods being located on opposed sides of the point around which said blade pivots.

15. A saw blade and cutting guide assembly, said assembly comprising:
- a saw blade assembly, said saw blade assembly including:
  - an elongated blade bar having opposed proximal and distal ends, the proximal end shaped to be attached to a saw and the distal end having a thickness, said blade bar further shaped to have an opening;
  - a blade having a base that is moveably mounted in said bar adjacent the bar distal end and a head integral with said base that has a thickness at least equal to the thickness of the bar distal end and teeth; and
  - at least one drive rod moveably disposed in said bar, said at least one drive rod having a proximal end shaped to be attached to a driver integral with the saw and a distal end connected to said blade base so that the actuation of said drive rod by the saw driver results in said drive rod oscillating said blade around a pivot point; and
- a cutting guide, said cutting guide comprising:
  - a body shaped to be positioned against tissue to be cut, said body having:
    - a guide surface;
    - a pin, said pin mounted to said body so as to extend above the guide surface, said pin dimensioned to seat in the saw blade assembly bar opening and said pin having a head that extends over said bar wherein, said saw blade assembly bar opening and said pin are collectively shaped so that said saw blade assembly bar is able to both move back and forth relative to said pin and pivot around said pin; and
  - features for receiving fasteners that hold said body to the tissue against which the body is positioned.

16. The saw blade and cutting guide assembly of claim 15, wherein said pin is mounted to said cutting guide so that said pin is able to move along the guide surface.

17. The saw blade and cutting guide assembly claim 15, wherein:
- said pin is removable attached to a complementary feature integral with said cutting guide body; and
- said cutting guide body is provided with plural features to which said pin can be attached so that said pin can be mounted to said body at plural locations on said body.

18. The saw blade and cutting guide assembly of claim 15, wherein said saw blade assembly bar and said pin are collectively formed so that said saw blade assembly bar can be detached from said cutting guide.

19. The saw blade and cutting guide assembly of claim 15, wherein said cutting guide is formed so that at least a portion of said guide surface is exposed.

20. The saw blade and cutting guide assembly of claim 15, wherein said saw blade assembly includes two said drive rods that extend from said blade base through said bar, said drive rods being located on opposed sides of the point around which said blade pivots.

21. The saw blade and cutting guide assembly of claim 15, wherein:
- said cutting guide body is shaped so that said guide surface is defined by an outer perimeter; and
- said cutting guide has at least one feature for receiving said pin that is located inward of the outer perimeter of the guide surface.

* * * * *